US007919609B2

(12) United States Patent
Boets et al.

(10) Patent No.: US 7,919,609 B2
(45) Date of Patent: Apr. 5, 2011

(54) TOXINS

(75) Inventors: Annemie Boets, Velzeke (BE); Greta Arnaut, Knesselare (BE); Jeroen Van Rie, Eeklo (BE); Nicole Damme, Krushausern (BE)

(73) Assignee: Bayer BioScience N.V., Ghent (BE)

( * ) Notice: Subject to any disclaimer, the term of this patent is extended or adjusted under 35 U.S.C. 154(b) by 0 days.

(21) Appl. No.: 11/503,355

(22) Filed: Aug. 10, 2006

(65) Prior Publication Data

US 2007/0056061 A1 Mar. 8, 2007

Related U.S. Application Data

(62) Division of application No. 10/682,915, filed on Oct. 14, 2003, now Pat. No. 7,091,399, which is a division of application No. 09/858,525, filed on May 17, 2001, now Pat. No. 6,706,860.

(60) Provisional application No. 60/304,164, filed on May 18, 2000.

(51) Int. Cl.
*C07H 21/04* (2006.01)
*A61K 38/00* (2006.01)

(52) U.S. Cl. ...................... 536/23.7; 536/23.1; 536/23.4

(58) Field of Classification Search ........................ None
See application file for complete search history.

(56) References Cited

U.S. PATENT DOCUMENTS

| | | | |
|---|---|---|---|
| 5,045,314 | A | 9/1991 | Bone et al. |
| 5,055,293 | A | 10/1991 | Aronson et al. |
| 5,455,028 | A | 10/1995 | O'Donnell |
| 5,645,831 | A | 7/1997 | Chilcott et al. |
| 5,702,701 | A | 12/1997 | O'Donnell |
| 5,849,870 | A | 12/1998 | Warren et al. |
| 5,877,012 | A | 3/1999 | Estruch et al. |
| 5,906,818 | A | 5/1999 | Heins et al. |
| 5,990,383 | A | 11/1999 | Warren et al. |
| 6,001,637 | A | 12/1999 | Heins et al. |
| 6,015,553 | A | 1/2000 | Germida et al. |
| 6,023,013 | A | 2/2000 | English et al. |
| 6,204,435 | B1 | 3/2001 | Feitelson et al. |
| 6,242,669 | B1 | 6/2001 | Feitelson et al. |
| 6,291,156 | B1 | 9/2001 | Estruch et al. |
| 6,297,369 | B1 | 10/2001 | Schnepf et al. |
| 6,501,099 | B2 | 12/2002 | Romano |
| 2002/0100080 | A1 | 7/2002 | Feitelson et al. |
| 2002/0120114 | A1 | 8/2002 | Schnepf et al. |

FOREIGN PATENT DOCUMENTS

| | | |
|---|---|---|
| WO | WO 94/21795 | 9/1994 |
| WO | WO 96/10083 | 4/1996 |
| WO | WO 9610083 A1 * | 4/1996 |
| WO | WO 97/26339 | 7/1997 |
| WO | WO 97/40162 | 10/1997 |
| WO | WO 97/46105 | 12/1997 |
| WO | WO 98/18932 | 5/1998 |
| WO | WO 98/44137 | 10/1998 |
| WO | WO 99/57282 | 11/1999 |
| WO | WO 9957282 A2 * | 11/1999 |
| WO | WO 00/09697 | 2/2000 |
| WO | WO 00/26378 | 5/2000 |

OTHER PUBLICATIONS

Schein et al. (2001) Chloroplast transit peptide prediction: a peek inside the black box, NUcleic acids Res., vol. 29, No. 16, e82, pp. 1-6.*
Kumar et al. (1999)Analysis of mutations in the pore-forming region essential for insecticidal activity of a *Bacillus thuringiensis* delta-endotoxin, J. Bacteriol., vol. 181, No. 19, pp. 6103-6107.*

Shan et al. (2005) Identification and analysis of multivalent proteolytically resistant peptides from gluten: implications for celiac sprue, J. Proteome. Res., vol. 4, No. 5, pp. 1732-1741.*

Coleoptera website (2008, updated) "Coleoptera, beetles", http://tolweb.org/Coleoptera, pp. 1-5, accessed on internet on Nov. 12, 2008.*

Orlova et al., "*Insecticidal Activity of Bacillus laterosporus*", 64(7) Applied and Environmental Microbiology pp. 2723-2725, American Society for Microbiology, Washington, D.C. USA.

Promega Protocols and Applications Guide, Second edition, Copyright 1991 (March) Promega Corporation, Madison, WI, USA, Cover page and pp. 69 and 401.

Betz et al. Regulartory and Toxicology and Pharmacology, vol. 32, pp. 156-173 (2000).

Sloderbeck, Phil et al. "Current Status of BT Corn Hybrids" dated Nov. 9, 2005 downloaded from http://www.oznet.ksu.edu/swao/Entomology/Bt_Folder/Bt%20Corns.html on Nov. 18, 2005.

* cited by examiner

*Primary Examiner* — Anand U Desai
*Assistant Examiner* — Samuel Liu
(74) *Attorney, Agent, or Firm* — Buchanan Ingersoll & Rooney PC

(57) ABSTRACT

Novel bacterial insecticidal proteins and equivalents thereof were isolated. These proteins and the DNA sequences encoding them are useful to make insecticidal compositions or transgenic plants to protect plants from damage by insects, particularly coleopteran insects.

11 Claims, No Drawings

TOXINS

BACKGROUND OF THE INVENTION

1. Field of the Invention

The present invention relates to new insecticidal secreted proteins ("ISPs") isolated from a bacterial strain, preferably a *Brevibacillus* species strain, most preferably a *Brevibacillus laterosporus* species strain which are insecticidal when ingested in combination with an ISP-complimentary protein such as another ISP protein of this invention, and to DNA sequences encoding such proteins. These proteins are useful to prevent or minimize insect damage, particularly of corn rootworms, to plants in a field.

The present invention also relates to plants, particularly corn plants, that are rendered insecticidal, preferably to coleopteran insects, particularly to *Diabrotica* spp., *Leptinotarsa* spp. and *Anthonomus* species insects, by the expression of the ISP proteins of this invention in cells of said plants.

The present invention also relates to a method for controlling damage by *Diabrotica* spp., *Leptinotarsa* spp. or *Anthonomus* species insects, preferably *Diabrotica* spp. insect pests, particularly corn rootworms, by having the ISP proteins of the invention, particularly the proteins with the amino acid sequence of any one of SEQ ID NO: 2, 4, 8 or 10, or insecticidally-effective fragments thereof, ingested by said insects.

2. Description of the Prior Art

Some of the most destructive pests are found among the Diabroticine beetles. In North America, the three important species of corn rootworms, *Diabrotica virgifera* (the Western corn rootworm), *Diabrotica barberi* (the Northern corn rootworm) and *Diabrotica undecimpunctata howardi* (the Southern corn rootworm) are considered to be the most expensive insect pests to control (Metcalf, 1986, Foreword in "Methods for the Study of Pest *Diabrotica*", pp. vii-xv, eds. Krysan, J. L. and Miller, T. A., Springer-Verlag, New York). *Diabrotica virgifera* and *Diabrotica barberi* are considered the most serious insect pests of corn in the major corn-producing states of the United States and Canada (Levine and Oloumi-Sadeghi, 1991, Annu. Rev. Entomol. 36, 229-55). The larvae feed on the roots and thus cause direct damage to corn growth and corn yields. Costs for soil insecticides to control larval damage to the root systems of corn and aerial sprays to reduce beetle damage to corn silks, when combined with crop losses, can approach one billion dollars annually (Metcalf, 1986, supra). Recently, in some US states it was discovered that the crop rotation program of planting soybeans after corn lost its effect as corn rootworms have adapted to this situation.

Bacterial strains and/or genes with toxicity to corn rootworm have been described in U.S. Pat. Nos. 6,023,013; 6,015,553; 6,001,637; 5,906,818; and 5,645,831. Also, PCT publications WO 00/09697, WO 99/57282, WO 98/18932, WO 97/40162, and WO 00/26378 relate to toxins and genes obtainable from *Bacillus* or other bacterial spp., some of which are described to have toxicity to corn rootworm. WO 98/44137, WO 94/21795 and WO 96/10083 relate to pesticidal *Bacillus* strains, characterized by pesticidal proteins and auxiliary proteins produced during vegetative growth, some of which are described to have toxicity to corn rootworm. U.S. Pat. No. 5,055,293 describes a method to control corn rootworms by inoculating soil with parasporal-inclusion forming species of *Bacillus laterosporus*.

Orlova et al. (1998, Applied Environmental Microbiol. 64, 2723) showed insecticidal activity to mosquitoes associated with protein crystals in crystal-forming strains of *Bacillus laterosporus*.

OBJECTS AND SUMMARY OF THE INVENTION

An object of the present invention is to provide novel proteins and DNA sequences encoding such proteins with significant toxicity to insects, preferably *Diabrotica* spp. insects, particularly corn rootworm.

In one embodiment of the invention, a protein is provided comprising the amino acid sequence of the smallest active toxin of the protein of SEQ ID NO: 2, wherein said smallest active toxin is:
a) a fragment of the protein of SEQ ID NO: 2, and
b) insecticidal to *Diabrotica virgifera* larvae when ingested by said larvae in combination with the protein of SEQ ID NO: 4 from amino acid position 51 to 457. Also provided is a protein comprising the amino acid sequence of the smallest active toxin of the protein of SEQ ID NO: 4, wherein said smallest active toxin is:
a) a fragment of the protein of SEQ ID NO: 4, and
b) insecticidal to *Diabrotica virgifera* larvae when ingested by said insect in combination with the protein of SEQ ID NO: 2 from amino acid position 38 to 871.

Particularly preferred is a protein characterized by an amino acid sequence comprising the sequence of SEQ ID NO: 2 from amino acid position 38 to amino acid position 768 or 781, preferably the protein characterized by the amino acid sequence of SEQ ID NO: 2 or SEQ ID NO: 10; and a protein characterized by an amino acid sequence comprising the sequence of SEQ ID NO: 4 from amino acid position 51 to amino acid position 449 or 457, preferably a protein characterized by the amino acid sequence of SEQ ID NO: 4 or SEQ ID NO: 8.

A further object of the invention is a protein comprising the amino acid sequence of the protease-digestion fragment of the protein encoded by the isp1A DNA deposited at the BCCM-LMBP under accession number LMBP 4009, which protease-digestion fragment is insecticidal to *Diabrotica virgifera* upon combined application with the protein of SEQ ID. No. 4 from amino acid position 51 to amino acid position 457; and a protein comprising the amino acid sequence of the protease-digestion fragment of the protein encoded by the isp2A DNA deposited at the BCCM-LMBP under accession number LMBP 4009, which protease-digestion fragment is insecticidal to *Diabrotica virgifera* upon combined application with the protein of SEQ ID NO: 2 from amino acid position 38 to amino acid position 871; particularly wherein said protease-digestion fragment is obtainable by treatment with coleopteran gut juice.

Also provided in accordance with this invention is a DNA sequence encoding the above proteins, particularly a DNA comprising an artificial DNA sequence having a different codon usage compared to the naturally occurring DNA sequence but encoding the same protein sequence, preferably contained in a chimeric gene operably linked to a plant-expressible promoter region (i.e., a promoter region which is suitable for expression in plant cells, this can be from bacterial, viral or plant origin or can be artificially made); particularly a promoter region which is preferentially active in root tissue.

In one embodiment of the invention, the promoter in said chimeric gene comprises the DNA sequence of SEQ ID NO: 5 or 6 or a DNA hybridizing thereto under stringent hybridization conditions.

In a further embodiment of this invention, the chimeric gene further comprises a signal peptide for secretion from the cell or for targeting to a cellular organelle, particularly a chloroplast transit peptide.

Also provided is a plant cell, a plant or a seed, comprising any of these chimeric genes integrated in their cells, particularly a combination of the chimeric gene encoding the ISP1A, or an insecticidally effective fragment thereof, and the chimeric gene encoding the ISP2A protein, or an insecticidally effective fragment thereof; particularly a corn cell, plant or seed.

In another embodiment of this invention, a micro-organism transformed to contain any of the above DNA sequences is provided.

Also provided is a process for controlling insects, particularly a process for rendering a plant resistant to coleopteran insects, comprising expressing any of the ISP proteins of this invention in cells of a plant, and regenerating transformed plants from said cells which are resistant to insects. In such process, the insect is preferably selected from the group consisting of: rootworms, weevils, potato beetles, *Diabrotica* species, *Anthonomus* spp., *Leptinotarsa* spp., *Agelastica alni, Hypera postica, Hypera brunneipennis, Haltica tombacina, Anthonomus grandis, Tenebrio molitor, Triboleum castaneum, Dicladispa armigera, Trichispa serica, Oulema oryzae, Colaspis brunnea, Lissorhorptrus oryzophilus, Phyllotreta cruciferae, Phyllotreta striolata, Psylliodes punctulata, Entomoscelis americana, Meligethes aeneus, Ceutorynchus* sp., *Psylliodes chrysocephala, Phyllotreta undulata, Leptinotarsa decemlineata, Diabrotica undecimpunctata, Diabrotica undecimpunctata howardi, Diabrotica barberi*, and *Diabrotica virgifera*.

Yet another object of the present invention is to provide a method for rendering plants insecticidal against Coleoptera and a method for controlling Coleoptera, comprising planting, sowing or growing in a field plants transformed with DNA sequences encoding the ISP proteins of the invention, particularly corn plants. In an embodiment of this invention, the ISP proteins are combined with other insecticidal proteins or protein combinations, preferably corn rootworm-toxic proteins.

Also provided in accordance with this invention are ISP1A or ISP2A equivalents, preferably from a *Brevibacillus laterosporus* strain, particularly from a *Brevibacillus laterosporus* strain not forming crystalline inclusions. Such equivalents preferably have molecular weights of about 95 to about 100 kD for ISP1A equivalents, and about 45 to about 50 kD for ISP2A equivalents, as determined in standard 8-10% SDS-PAGE gel electrophoresis using appropriate molecular weight markers.

DETAILED DESCRIPTION OF THE PREFERRED EMBODIMENTS OF THE INVENTION

In accordance with this invention, new bacterial toxins and DNA sequences encoding them have been isolated and characterized. The new proteins were designated ISP1A and ISP2A, and the DNA sequences encoding them isp1A and isp2A.

In accordance with this invention "ISP1A protein" refers to any protein comprising the smallest protein fragment of the amino acid sequence of SEQ ID NO: 2 which retains insecticidal activity, particularly to coleopteran insects, more particularly to corn rootworm, cotton boll weevil and Colorado potato beetle, preferably to *Diabrotica* spp., especially to Southern, Western and Northern corn rootworm, particularly to *Diabrotica virgifera*, upon combined ingestion by an insect with a suitable ISP-complimentary protein, particularly the mature ISP2A protein. This includes any protein with an amino acid sequence comprising the amino acid sequence from the amino acid at position 32 or 38, preferably 38, to an amino acid at a position from amino acid position 768 to amino acid position 871 in SEQ ID NO: 2, particularly any protein with an amino acid sequence comprising at least the amino acid sequence of SEQ ID NO: 2 from amino acid position 38 to amino acid position 768. This also includes the protein obtained from the amino acid sequence of SEQ ID NO: 2 by cleaving off part or all of the N-terminal signal peptide sequence or the protein wherein the signal peptide sequence has been replaced by another, e.g. a plant, targeting peptide, a methionine amino acid or a methionine-alanine dipeptide. Specifically, this includes the protein comprising an N-terminal prokaryotic or eucaryotic, e.g. bacterial or plant, signal peptide for secretion or targeting. This also includes hybrids or chimeric proteins comprising the above described smallest toxic protein fragment, e.g., a hybrid between an ISP1A and ISP2A protein of this invention. Further, included in the designation "ISP1A", as used herein, are also protease-resistant fragments of the ISP1A protein retaining insecticidal activity obtainable by treatment with insect gut juice, preferably coleopteran gut juice, particularly coleopteran gut proteases, preferably corn rootworm proteases, e.g., cysteine proteinases, serine proteinases, trypsin, chymotrypsin or trypsin-like proteases. Particularly, the coleopteran is selected from the group consisting of: corn rootworm, cotton boll weevil and Colorado potato beetle, *Diabrotica* spp., *Diabrotica virgifera, Diabrotica barberi, Diabrotica undecimpuncata, Leptinotarsa decemlineata*, and *Anthonomus grandis*. In a preferred embodiment of this invention, an ISP1A protein according to this invention is not insecticidal when ingested in isolation without providing simultaneously or sequentially, an ISP complimentary protein such as an ISP2A protein.

In accordance with this invention "ISP2A protein" refers to any protein comprising the smallest protein fragment of the amino acid sequence of SEQ ID NO: 4 which retains insecticidal activity, particularly to coleopteran insects, more particularly to corn rootworm, cotton boll weevil and Colorado potato beetle, preferably to *Diabrotica* spp., especially to *Diabrotica virgifera, Diabrotica barberi, Diabrotica undecimpuncata*, upon combined ingestion by an insect with a suitable ISP-complimentary protein, particularly the mature ISP1A protein. This includes any protein with an amino acid sequence comprising the amino acid sequence from the amino acid at position 43 or 51, preferably 51, to the amino acid at a position from amino acid position 449 to position 457 in SEQ ID NO: 4, particularly any protein with an amino acid sequence comprising at least the amino acid sequence of SEQ ID NO: 4 from amino acid position 51 to position 449. This also includes the protein obtained from the amino acid sequence of SEQ ID NO: 4 by cleaving off part or all of the N-terminal signal peptide sequence of the protein, and the protein wherein the signal peptide has been replaced by another, e.g., a plant, targeting peptide, a methionine amino acid or a methionine-alanine dipeptide. Specifically, this includes the protein comprising an N-terminal prokaryotic or eucaryotic, e.g. bacterial or plant, signal peptide for secretion or targeting. This also includes hybrids or chimeric proteins comprising the above described smallest toxic protein fragment, e.g., a hybrid between an ISP1A and ISP2A protein of this invention. Further, included in the designation "ISP2A", as used herein, are also protease-resistant fragments of the ISP2A protein retaining insecticidal activity obtainable by treatment with insect gut juice, preferably coleopteran gut juice, particularly coleopteran gut proteases, e.g., cysteine proteinases, serine proteinases, trypsin, chymotrypsin or trypsin-like proteases. In a preferred embodiment of this invention, an ISP2A protein according to this invention is not insecticidal when ingested in isolation without providing simultaneously or sequentially, an ISP complimentary protein such as an ISP1A protein.

An "ISP-complimentary protein", as used herein, refers to a protein, including but not limited to the mature ISP1A or ISP2A protein, which in combination with one of the ISP proteins of this invention, is insecticidal upon ingestion by an insect, particularly a coleopteran insect, preferably a corn rootworm, a cotton boll weevil or Colorado potato beetle, more particularly *Diabrotica virgifera*, *Diabrotica barberi*, *Diabrotica undecimpuncata* or *Anthonomus grandis*. Particularly, also VIP ("Vegetative Insecticidal Proteins") proteins and active fragments thereof, particularly the mature VIP proteins with their signal sequences cleaved off, as described in WO 98/44137, WO 94/21795 and WO 96/10083 are ISP-complimentary proteins in accordance with this invention. An ISP-complimentary protein to the ISP1A protein is ideally the ISP2A protein or the VIP2Aa or VIP2Ab protein or active fragments thereof (such as the mature proteins with the signal sequences removed) as described in U.S. Pat. No. 5,990,383, or any bacterial secreted protein which has a sequence identity of at least 50%, preferably at least 75%, particularly at least 85%, to any one of the ISP2 or VIP2 proteins, and which is insecticidal when ingested by an insect, preferably a coleopteran insect, particularly a corn rootworm, in combination with the mature ISP1A protein. An ISP-complimentary protein to the ISP2A protein is ideally the mature ISP1A protein, the VIP1Aa or VIP1Ab protein or active fragments thereof (such as the mature protein with the signal peptide removed) as described in U.S. Pat. No. 5,990,383, or any bacterial secreted protein which has a sequence identity of at least 50%, preferably at least 75%, particularly at least 85%, to any one of the ISP1 or VIP1 proteins, and which is insecticidal when ingested by an insect, preferably a coleopteran insect, particularly a corn rootworm, in combination with the mature ISP2A protein. For the avoidance of doubt, an ISP-complimentary protein and an ISP protein are always different proteins.

In a preferred embodiment of this invention, the ISP proteins of this invention, or their equivalents, when used in isolation, i.e., without any of the complementary ISP proteins present, do not result in any significant insecticidal activity, preferably to corn rootworm larvae, particularly to *Diabrotica virgifera*, when tested in a surface contamination assay on standard insect diet, and this at a concentration wherein the proteins (each applied in that concentration) in combination result in 100% mortality, preferably to corn rootworm larvae, particularly to *Diabrotica virgifera*. Particularly, the ISP1 proteins of this invention give no significant mortality (i.e., no difference with the controls using a buffer solution alone) to *Diabrotica virgifera* larvae when only an ISP1 protein is applied at a concentration of 70 ng/cm2 in a surface contamination assay using standard corn rootworm diet, and the ISP2 proteins of this invention give no significant mortality (i.e., no difference with the controls using a buffer solution alone) to *Diabrotica virgifera* larvae when only an ISP2 protein is applied at a concentration of 36 ng/cm2 in a surface contamination assay using standard corn rootworm diet, while ISP1 and ISP2 proteins applied together in these concentrations in the same type of assay give 100% mortality to these larvae.

As used herein, "ISP1A equivalent" or "ISP2A equivalent" refers to a protein with the same or substantially the same toxicity to a target insect as the ISP1A or ISP2A protein, respectively, when applied to such target insect, preferably when ingested by such insect, in a binary combination with an ISP-complimentary protein, and with substantially the same amino acid sequence as the ISP1A or ISP2A protein, respectively. Also included in the definition of ISP1A or ISP2A equivalents are bacterial proteins of respectively about 45 to about 50 kD and about 95 to about 100 kD molecular weight as determined by standard 8-10% SDS-PAGE gel electrophoresis, preferably from a *Brevibacillus laterosporus* strain, particularly from a *Brevibacillus laterosporus* strain not forming crystalline inclusions, which proteins in combination but not in isolation, have significant insecticidal activity to corn rootworm larvae.

The use of the terms "in combination", when referring to the application of an ISP protein (or its equivalent) and an ISP-complimentary protein to a target insect to get an insecticidal effect, includes the simultaneous application (i.e., in the same feed, cells or tissue and applied or ingested by an insect at the same moment) and the separate, sequential application (i.e. one is provided after the other but not applied or ingested at the same time) of an ISP protein (or its equivalent) and an ISP-complimentary protein of this invention, as long as these proteins are found together in the insect gut at one moment in time. The ISP1A protein of this invention could thus be expressed in a certain type of cells or a certain zone in the roots of a plant, while the ISP2A protein of this invention could be expressed in another kind of cells or another zone in the roots of the same plant, so that the proteins will only interact once root material is ingested. Also included herein is the expression of an ISP protein or its equivalent in roots of a plant, particularly a corn plant, and the expression of an ISP-complimentary protein in root-associated bacteria such as rhizobacteria strains (or vice versa).

"The same toxicity to a target insect", with respect to an ISP protein and an ISP equivalent protein as used herein, means that the mean mortality of the ISP protein, in the presence of a suitable ISP-complimentary protein, is not significantly different from the mean mortality of the ISP equivalent, also in the presence of the same suitable ISP-complimentary protein. Particularly, this refers to the situation wherein the 95% fiducial limits of the LC50 of the ISP protein (when tested in the presence of a suitable ISP-complimentary protein) overlap with the 95% fiducial limits of the LC50 of the ISP equivalent (when tested in the presence of a suitable ISP-complimentary protein).

"Substantially the same toxicity to a target insect", as used herein with respect to an ISP protein and an ISP equivalent protein, refers to levels of mean mortality of such proteins to a target insect which are significantly different between the ISP and the ISP equivalent protein, but which are still within a range of insecticidal activity which is useful to control or kill the relevant target insect, preferably when such protein is expressed in a plant. In a preferred embodiment of this invention, proteins have substantially the same toxicity to a target insect when their LC50 values for such a target insect in the same (replicated) in vitro assay conducted under the same assay conditions differ from each other by a factor 2 to 100, preferably 2 to 50, particularly 2 to 20, most preferably 2 to 10.

Also, functionally analogous amino acids can be used to replace certain amino acids in an ISP1A or ISP2A protein to obtain ISP1A or ISP2A equivalents. For example, one or more amino acids within the sequence can be substituted by other amino acids of a similar polarity which act as a functional equivalent, resulting in a silent alteration with respect to functionality of the protein. Substitutes for an amino acid within the sequence can be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Proteins wherein conservative amino acids replacements are made using amino acids of the above indicated same class which retain substantially the same insecticidal activity to a target insect compared to the original protein, are included herein as equivalents of the ISP proteins of this invention.

A protein with "substantially the same amino acid sequence" to an ISP1A protein, as used herein, refers to a protein with at least 90%, particularly at least 95%, preferably at least 97% sequence identity with the ISP1A protein, wherein the percentage sequence identity is determined by using the blosum62 scoring matrix in the GAP program of the Wisconsin package of GCG (Madison, Wis., USA) version 10.0 (GCG defaults used). "Sequence identity", as used throughout this application, when related to proteins, refers to the percentage of identical amino acids using this specified analysis. The "sequence identity", as used herein, when related to DNA sequences, is determined by using the nwsgapdna scoring matrix in the GAP program of the Wisconsin package of GCG (Madison, Wis., USA) version 10.0 (GCG defaults used).

"ISP protein" or "ISP protein of this invention", as used herein, refers to any one of the new proteins of this invention and identified herein as ISP1A or ISP2A protein or their equivalents. An "ISP protoxin" refers to the full length ISP1A or ISP2A protein as it is encoded by the naturally-occurring bacterial DNA sequence, including the signal peptide. An "ISP toxin" refers to an insecticidal fragment thereof, particularly the smallest toxic fragment thereof or the mature protein with the signal peptide removed. A "mature" ISP, as used herein, refers to the ISP protein of this invention as secreted by its native bacterial host cell which is insecticidally active in combination with an ISP-complimentary protein (without the N-terminal bacterial signal peptide sequence). A mature ISP protein can have a complete native C-terminal or can have a C-terminal truncation.

Also included in this invention as an ISP protein is a first protein with an apparent molecular weight of its mature form of about 95 to about 100 kD, particularly about 100 kD, which is secreted by a bacterium, preferably a bacterium which is not *B. thuringiensis* or *B. cereus*, particularly a bacterium which is *Brevibacillus laterosporus*, or insecticidally effective fragments of said first protein, characterized by a significant insecticidal activity when combined with a second protein with an apparent molecular weight of its mature form of about 45 to about 50 kD, preferably about 45 kD, which is secreted by a bacterium, preferably a bacterium which is not *B. thuringiensis* or *B. cereus*, particularly a bacterium which is *Brevibacillus laterosporus*, or insecticidally effective fragments of said second protein, wherein the combination of said first and said second protein, or their insecticidal fragments, is significantly insecticidal to larvae of the Colorado potato beetle, the Western corn rootworm, the Southern corn rootworm, and the Northern corn rootworm, when ingested by said insects, and wherein said protein combination is not significantly insecticidal to *Ostrinia nubilalis, Spodoptera frugiperda, Heliothis virescens, Helicoverpa zea* and *Sesamia nonagroides*, when ingested by said insects, and wherein said first protein alone has no significant insecticidal activity when ingested by an insect. Also included herein is the second protein as described above which is insecticidal when ingested by an insect in combination with the above described first protein.

"Apparent molecular weight", as used herein, is the molecular weight as evidenced by SDS-PAGE analysis upon comparison with molecular weight standards. As is appreciated by the skilled person, this molecular weight is an approximate determination and can have a range of variation of about 10-15% with respect to the actual molecular weight as determined based on the amino acid sequence.

As used herein, the terms "isp1A DNA" or "isp2A DNA" refer to any DNA sequence encoding the ISP1A or ISP2A protein, respectively, as defined above. This includes naturally occurring, artificial or synthetic DNA sequences encoding the newly isolated proteins or their fragments as defined above, particularly DNA sequences with a modified codon usage adapted to more closely match the codon usage of a plant. Examples of artificial DNA sequences encoding an ISP1A and ISP2A protein are shown in SEQ ID Nos. 9 and 7, respectively (the ISP proteins encoded by these DNA sequences are defined herein as ISP1A-1 and ISP2A-1). Also included herein are DNA sequences encoding insecticidal proteins which are similar enough to the DNA sequence of SEQ ID NO: 1, 3, 7 or 9 so that they can (i.e., have the ability to) hybridize to these DNA sequences under stringent hybridization conditions. "Stringent hybridization conditions", as used herein, refers particularly to the following conditions wherein hybridization is still obtained: immobilizing a first DNA sequence on filters, and prehybridizing the filters for either 1 to 2 hours in 50 formamide, 5% SSPE, 2×Denhardt's reagent and 0.1% SDS at 42° C. or 1 to 2 hours in 6×SSC, 2×Denhardt' s reagent and 0.1% SDS at 68° C. The denatured radiolabeled second DNA is then added directly to the prehybridization fluid and incubation is carried out for 16 to 24 hours at one of the above selected temperatures. After incubation, the filters are then washed for 20 minutes at room temperature in 1×SSC, 0.1% SDS, followed by three washes of 20 minutes each at 68° C. in 0.2×SSC and 0.1% SDS. An autoradiagraph is established by exposing the filters for 24 to 48 hours to X-ray film (Kodak XAR-2 or equivalent) at −70° C. with an intensifying screen. Of course, equivalent conditions and parameters can be used in this process while still retaining the desired stringent hybridization conditions. As used herein, stringent hybridization preferably occurs between DNA sequences with at least 90 to 95%, preferably at least 97%, particularly 99%, sequence identity.

Also included in the definition of "isp1 DNA" are all DNA sequences encoding a protein with a sequence identity of at least 90%, preferably at least 95%, particularly at least 97%, most preferably at least 99% with the protein of SEQ ID. No. 2 and which has substantially the same, preferably the same, insecticidal activity of the protein of SEQ ID NO: 2, wherein said protein sequence identity is determined by using the blosum62 scoring matrix in the GAP program of the Wisconsin package of GCG (Madison, Wis., USA) version 10.0 (GCG defaults used). Included in the definition of "isp2 DNA" are all DNA sequences encoding a protein with a sequence identity of at least 90%, preferably at least 95%, particularly at least 97%, most preferably at least 99%, with the protein of SEQ ID. No. 4 and which has substantially the same, preferably the same, insecticidal activity of the protein of SEQ ID NO: 4, wherein said protein sequence identity is determined by using the blosum62 scoring matrix in the GAP program of the Wisconsin package of GCG (Madison, Wis., USA) version 10.0 (GCG defaults used).

An "isp gene" or "isp DNA", as used herein, is a DNA sequence encoding an ISP protein in accordance with this invention, referring to any one of the isp1A or isp2A DNA sequences defined above.

An "isp DNA equivalent" or an "isp gene equivalent", as used herein, is a DNA encoding an ISP equivalent protein as defined above.

The terms "DNA/protein comprising the sequence X" and "DNA/protein with the sequence comprising sequence X", as used herein, refer to a DNA or protein including or containing at least the sequence X in their nucleotide or amino acid sequence, so that other nucleotide or amino acid sequences can be included at the 5' (or N-terminal) and/or 3' (or C-terminal) end, e.g., an N-terminal transit or signal peptide. The term "comprising", as used herein, is open-ended language in the meaning of "including", meaning that other elements then those specifically recited can also be present. The term "consisting of", as used herein, is closed-ended language, i.e., only those elements specifically recited are present. The term "DNA encoding a protein comprising sequence X", as used herein, refers to a DNA comprising a coding sequence which after transcription and translation results in a protein containing at least amino acid sequence X. A DNA encoding a protein need not be a naturally-occurring DNA, and can be a semi-synthetic, fully synthetic or artificial DNA and can include introns and 5' and/or 3' flanking regions. The term "nucleotide sequence", as used herein, refers to the sequence of a DNA or RNA molecule, which can be in single- or double-stranded form.

The term "gene", as used herein refers to a DNA coding region flanked by 5' and/or 3' regulatory sequences allowing an RNA to be transcribed which can be translated to a protein, typically comprising at least a promoter region. A "chimeric gene", when referring to an isp DNA of this invention, refers to an isp DNA sequence having 5' and/or 3' regulatory sequences different from the naturally-occurring bacterial 5' and/or 3' regulatory sequences which drive the expression of the ISP protein in its native host cell.

"Insecticidal activity" or "insecticidally effective", when referring to an ISP protein of the invention or its equivalents, as used herein, means the capacity of an ISP protein to kill insects above the levels found in control treatment under the same assay conditions, upon the ingestion of such protein by an insect, preferably a coleopteran insect, particularly a corn rootworm, especially *Diabrotica virgifera*, in combination with an ISP-complimentary protein, such as a second ISP protein. Preferably the second ISP protein is the other protein encoded by the same bacterial operon as the first ISP or an insecticidally-effective fragment or equivalent thereof, yielding optimal insect mortality upon ingestion of the combined proteins. "Insect-controlling amounts" of an ISP protein, as used herein, refers to an amount of ISP protein which is sufficient to limit damage on a plant by insects feeding on such plant to commercially acceptable levels, e.g. by killing the insects or by inhibiting the insect is development or growth in such a manner that they provide less damage to a plant and plant yield is not significantly adversely affected, when such ISP protein is provided with an ISP-complimentary protein, such as another ISP protein, preferably the other protein encoded by the same operon as the first ISP, or an insecticidally effective fragment thereof. "Insecticidally-effective ISP fragment", as used herein, refers to a fragment of an ISP protein of this invention which retains insecticidal activity when provided in combination with an ISP-complimentary protein, such as another ISP protein, preferably the other ISP encoded by the same operon as the first ISP. In the above definitions related to insecticidal activity, the insect preferably is a larva in any of the larval stages. Throughout this application, reference can be made to an "isp DNA and insecticidally-effective fragments or equivalents thereof", and in that case the insecticidal activity obviously refers to the activity of the protein encoded by the DNA and not to the insecticidal activity of the DNA itself.

In accordance with this invention, the ISP proteins of this invention and their equivalents, particularly the mature ISP1A and ISP2A proteins, were found to have no significant insecticidal activity to lepidopteran insects selected from the group consisting of: *Heliothis virescens, Helicoverpa zea, Manduca sexta, Helicoverpa armigera, Spodoptera littoralis, Spodoptera frugiperda, Sesamia nonagroides*, and *Ostrinia nubilalis*.

In accordance with this invention, target insects susceptible to the ISP proteins of the invention or their equivalents are contacted with these proteins in insect-controlling amounts, preferably insecticidal amounts, by expression in a transgenic plant of DNA sequences encoding such ISP proteins. Said target insects will only be affected by the insecticidal proteins when they ingest plant tissue. Thus, in another object of the present invention a method is provided for rendering plants insecticidal against Coleoptera and a method for controlling Coleoptera, comprising planting, sowing or growing in a field plants transformed with DNA sequences encoding the ISP proteins of the invention, particularly corn plants.

The signal peptide of the ISP proteins of the invention can be removed or modified according to procedures known in the art, see, e.g., published PCT patent application WO 96/10083, or they can be replaced by another peptide such as a chloroplast transit peptide (e.g., Van Den Broeck et al., 1985, Nature 313, 358, or preferably the modified chloroplast transit peptide of U.S. Pat. No. 5,510,471) causing transport of the protein to the chloroplasts, by a secretory signal peptide or a peptide targeting the protein to other plastids, mitochondria, the ER, or another organelle, or it can be replaced by a methionine amino acid or by a methionine-alanine dipeptide. Signal sequences for targeting to intracellular organelles or for secretion outside the plant cell or to the cell wall are found in naturally targeted or secreted proteins, preferably those described by Klösgen et al. (1989, Mol. Gen. Genet. 217, 155-161), Klösgen and Weil (1991, Mol. Gen. Genet. 225, 297-304), Neuhaus & Rogers (1998, Plant Mol. Biol. 38, 127-144), Bih et al. (1999, J. Biol. Chem. 274, 22884-22894), Morris et al. (1999, Biochem. Biophys. Res. Commun. 255, 328-333), Hesse et al. (1989, EMBO J. 8 2453-2461), Tavladoraki et al. (1998, FEBS Lett. 426, 62-66), Terashima et al. (1999, Appl. Microbiol. Biotechnol. 52, 516-523), Park et al. (1997, J. Biol. Chem. 272, 6876-6881), Shcherban et al. (1995, Proc. Natl. Acad. Sci. USA 92, 9245-9249), all of which are incorporated herein by reference, particularly the signal peptide sequences from targeted or secreted proteins of corn. Although a DNA sequence encoding such a plant signal peptide can be inserted in the chimeric gene encoding the ISP1A and in the chimeric gene encoding the ISP2A protein for expression in plants, in one embodiment of this invention, a DNA sequence encoding such a signal peptide is only inserted in the chimeric ISP2A gene and the ISP1A chimeric gene lacks a signal peptide, or has a methionine amino acid or a methionine-alanine dipeptide instead of the signal peptide. In a preferred embodiment of this invention, the proteins are secreted from the roots as described by Gleba et al. (1999, Proc. Natl. Acad. Sci. USA 25, 5973-5977) and Borisjuk et al., 1999 (Nat. Biotechn. 17, 466-469), using a strong root-preferred promoter, particularly a strong root-preferred promoter from corn, and an N-terminal signal peptide for secretion from the root cells, preferably from corn, particularly the signal peptide of a secreted protein, preferably a corn secreted protein, selected from the group of: expansin, alpha-amylase, polyamine oxidase, cytokinin oxidase, endoxylanase.

Plants included in the scope of this invention are corn, cotton, soybean, peas, beans, lentils, potato, tomato, tobacco, lettuce, *Brassica* species plants, sugarcane, rice, oilseed rape, mustard, asparagus, wheat, barley, coffee, tea, vines, rubber plant, beet, turf grasses, sorghum, oats, rye, onions, carrots, leek, cucumber, squash, melon, sunflower, particularly any plant which is susceptible to damage by coleopteran insects, preferably corn rootworm, potato beetles or weevils, particularly insects of the *Diabrotica* or *Leptinotarsa* species, most preferably any insect selected from the group consisting of: *Diabrotica virgifera, Diabrotica barberi, Diabrotica undecimpuncata, Leptinotarsa decemlineata* and *Anthonomus grandis*, most preferably corn plants.

"Corn", as used herein, refers to all plants of the species *Zea mays*, and any seeds, roots or grain, or other materials containing or directly produced from corn cells, of any variety of *Zea mays*, including but not limited to field corn, sweet corn, hybrid corn, white corn and dent corn, whether hybrid or inbred lines. Preferably, the corn plants used in this invention are suitable parent lines for producing hybrid corn, and most preferably they already carry an endogenous or transgenic insect-resistance giving them protection from the major corn lepidopteran insect pests including but not limited to *Ostrinia nubilalis*.

The ISP1A and ISP2A proteins of this invention can be isolated in a conventional manner from the *E. coli* strain, deposited under the provisions of the Budapest Treaty on Jan. 11, 2000 at the BCCM-LMBP (Belgian Coordinated Collections of Microorganisms—Laboratorium voor Moleculaire Biologie—Plasmidencollectie, University of Gent, K. L. Ledeganckstraat 35, B-9000 Gent, Belgium) under accession number LMBP 4009, or more preferably, they can be isolated from the supernatant of a *Bacillus* strain, preferably a crystal-minus *Bacillus thuringiensis* strain, transformed with a plasmid containing the approximately 7 kb XbaI-EcoRI fragment of the plasmid pUCIB120/ISP as deposited under accession number LMBP 4009. The ISP proteins can be used to prepare specific monoclonal or polyclonal antibodies in a conventional manner (Höfte et al., 1988, Appl. Environm. Microbiol. 54, 2010). The ISP proteins can be treated with a protease such as cysteine proteases, to obtain the protease-resistant fragments of the ISP proteins.

The DNA sequences encoding the ISP proteins can be isolated in a conventional manner from the deposited strain or can be synthesized based on the encoded amino acid sequence.

DNA sequences encoding other ISP proteins in accordance with this invention can be identified by digesting total DNA from isolated bacterial strains with restriction enzymes; size fractionating the DNA fragments, so produced, into DNA fractions of 5 to 10 Kb, preferably 7 to 10 Kb; ligating these fractions to cloning vectors; screening the *E. coli*, transformed with the cloning vectors, with a DNA probe that was constructed from a region of known ISP protein genes or with a DNA probe based on specific PCR fragments generated from isp DNA using primers corresponding to certain regions within known ISP protein genes. Such "other ISP proteins" isolated in accordance with this invention, like the ISP proteins of this invention, are characterized by any or all, preferably all, of the following characteristics: a) their significant insecticidal activity to larvae of the Southern corn rootworm, *Diabrotica undecimpunctata*, and to larvae of the Colorado potato beetle, *Leptinotarsa decemlineata*, upon ingestion of such other ISP protein with an ISP-complimentary protein, preferably the mature ISP1A or ISP2A protein of this invention; b) their lack of significant insecticidal activity to larvae of lepidopteran insects, preferably *Ostrinia nubilalis*, upon ingestion of such other ISP protein with an ISP-complimentary protein, preferably the mature ISP1A or ISP2A proteins of this invention; c) their apparent molecular weight of about 100 kD or about 45 kD of the mature forms (without signal peptide), d) their occurrence in the supernatant of a bacterial strain culture which is not *Bacillus thuringiensis* or *Bacillus cereus*, and e) by their lack of significant toxicity to corn rootworms, preferably *Diabrotica virgifera*, upon ingestion in the absence of an ISP complimentary protein.

Of course, any other DNA sequence differing in its codon usage but encoding the same protein or a similar protein with substantially the same insecticidal activity, can be constructed, depending on the particular purpose. It has been described in some prokaryotic and eucaryotic expression systems that changing the codon usage to that of the host cell is desired for gene expression in foreign hosts (Bennetzen & Hall, 1982, J. Biol. Chem. 257, 3026; Itakura, 1977, Science 198, 1056-1063). Codon usage tables are available in the literature (Wada et al., 1990, Nucl. Acids Res. 18, 2367-1411; Murray et al., 1989, Nucleic Acids Research 17, 477-498) and in the major DNA sequence databases. Accordingly, synthetic DNA sequences can be constructed so that the same or substantially the same proteins are produced. It is evident that several DNA sequences can be devised once the amino acid sequence of the ISP proteins of this invention is known. Such other DNA sequences include synthetic or semi-synthetic DNA sequences that have been changed in order to inactivate certain sites in the gene, e.g. by selectively inactivating certain cryptic regulatory or processing elements present in the native sequence, or by adapting the overall codon usage to that of a more related host organism, preferably that of the host organism in which expression is desired. Synthetic DNA sequences could also be made following the procedures described in EP 0 385 962, EP 0 618 967, or EP 0 682 115.

Small modifications to a DNA sequence such as described above can be routinely made by PCR-mediated mutagenesis (Ho et al., 1989, Gene 77, 51-59; White et al., 1989, Trends in Genet. 5, 185-189). New synthetic or semi-synthetic genes can be made by automated DNA synthesis and ligation of the resulting DNA fragments.

To prevent or delay the development of resistance by coleopteran insects, particularly corn rootworm, cotton boll weevil or Colorado potato beetle, preferably *Leptinotarsa decemlineata, Diabrotica barberi, Diabrotica undecimpuncata, Anthonomus grandis* or *Diabrotica virgifera*, to transgenic hosts, particularly plants, expressing ISP proteins of this invention or their equivalents, it is preferred to also express in the same host, preferably a transgenic plant, another protein or another protein complex, which has a different mode of action, and a high toxicity to the same insect targeted by the first toxin or toxin complex when produced in a transgenic host, preferably a plant. Suitable candidates to be combined with the ISP1A and ISP2A of the invention include the mature VIP1Aa protein when combined with the mature VIP2Aa or VIP2Ab protein of PCT publication WO 96/10083 in case these VIP proteins have a different mode of action compared to the ISP proteins; the corn rootworm toxins of *Photorhabdus* or *Xenorhabdus* spp., e.g., the insecticidal proteins of *Photorhabdus luminescens* W-14 (Guo et al., 1999, J. Biol. Chem. 274, 9836-9842); the CryET70 protein of WO 00/26378; the insecticidal proteins produced by Bt strains PS80JJ1, PS149B1 and PS167H2 as described in WO 97/40162, particularly the about 14 kD and about 44 kD proteins of Bt strain PS149B1; the Cry3Bb protein of U.S. Pat. No. 6,023,013; protease inhibitors such as the N2 and R1 cysteine proteinase inhibitors of soybean (Zhao et al., 1996, Plant Physiol. 111, 1299-1306) or oryzastatine such as rice cystatin (Genbank entry S49967), corn cystatin (Genbank entries D38130, D10622, D63342) such as the corn cystatin expressed in plants as described by He et al. (1996, Plant Mol. Biol. 30, 149-157). Also included herein are all equivalents and variants, such as truncated proteins retaining insecticidal activity, of any of the above proteins.

Such combined expression can be achieved by transformation of a plant already transformed to express a corn rootworm toxic protein or protein complex, or by crossing plants transformed to express different corn rootworm toxic proteins. Alternatively, expression of the ISP proteins of the invention can be induced in roots upon feeding of corn rootworm larvae on root tissue, e.g., by using a wound-induced promoter region, preferably a wound-induced root-preferred promoter region.

The 5 to 10, preferably 7 to 10, Kb fragments, prepared from total DNA of the isp genes of the invention, can be ligated in suitable expression vectors and transformed in *E. coli*, and the clones can then be screened by conventional colony immunoprobing methods (French et al., 1986, Anal. Biochem. 156, 417-423) for expression of the toxin with monoclonal or polyclonal antibodies raised against the ISP proteins. Also, the 5 to 10 Kb fragments, prepared from total DNA of the bacterial strains of the invention, can be ligated in suitable Bt shuttle vectors (Lereclus et al., 1992, Bio/Technology 10, 418) and transformed in a crystal minus Bt-mutant. The clones are then screened for production of ISP proteins (by SDS-PAGE, Western blot and/or insect assay).

The genes encoding the ISP proteins of this invention can be sequenced in a conventional manner (Maxam and Gilbert, 1980, Methods in Enzymol. 65, 499-560; Sanger, 1977, Proc. Natl. Acad. Sci. USA 74, 5463-5467) to obtain the DNA sequence. Sequence comparisons indicated that the genes are different from previously described genes encoding proteins secreted during the vegetative growth phase of *Bacillus* or other bacterial species and *Bacillus thuringiensis* crystal proteins with activity against Coleoptera (Crickmore, et al., 1998, Microbiology and Molecular Biology Reviews Vol 62: 807-813; WO 98/44137, WO 94/21795, WO 96/10083, WO 00/09697, WO 9957282, and WO 9746105).

In order to express all or an insecticidally effective part of the DNA sequence encoding an ISP protein of this invention in *E. coli*, in other bacterial strains or in plants, suitable restriction sites can be introduced, flanking the DNA sequence. This can be done by site-directed mutagenesis, using well-known procedures (e.g., Stanssens et al., 1989, Nucleic Acids Research 12, 4441-4454; White et al., 1989, supra). For expression in plants, the isp DNA of the invention, or its equivalent, is usually contained in a chimeric gene, flanked by 5' and 3' regulatory sequences including a plant-expressible promoter region and 3' transcription termination and polyadenylation sequence active in plant cells. In order to obtain improved expression in plants, the codon usage of the isp DNA or its equivalent of this invention can be modified to form an equivalent, modified or artificial gene or gene part, or the isp DNA or insecticidally-effective parts thereof can be inserted in the chloroplast genome and expressed there using a chloropast-active promoter (e.g., Mc Bride et al., 1995, Bio/Technology 13, 362). For obtaining enhanced expression in monocot plants such as corn, a monocot intron also can be added to the chimeric gene, and the isp DNA sequence or its insecticidal part can be further changed in a translationally neutral manner, to modify possibly inhibiting DNA sequences present in the gene part by means of site-directed intron insertion and/or by introducing changes to the codon usage, e.g., adapting the codon usage to that most preferred by the specific plant (Murray et al., 1989, supra) without changing significantly the encoded amino acid sequence.

The insecticidally effective isp DNA or its equivalent, preferably the isp chimeric gene, encoding an ISP protein, can be stably inserted in a conventional manner into the nuclear genome of a single plant cell, and the so-transformed plant cell can be used in a conventional manner to produce a transformed plant that is insect-resistant. In this regard, a disarmed Ti-plasmid, containing the insecticidally effective isp gene part, in *Agrobacterium tumefaciens* can be used to transform the plant cell, and thereafter, a transformed plant can be regenerated from the transformed plant cell using the procedures described, for example, in EP 0 116 718, EP 0 270 822, PCT publication WO 84/02913 and published European Patent application ("EP") 0 242 246 and in Gould et al. (1991, Plant Physiol. 95, 426-434). Preferred Ti-plasmid vectors each contain the insecticidally effective isp chimeric gene sequence between the border sequences, or at least located to the left of the right border sequence, of the T-DNA of the Ti-plasmid. Of course, other types of vectors can be used to transform the plant cell, using procedures such as direct gene transfer (as described, for example in EP 0 233 247), pollen mediated transformation (as described, for example in EP 0 270 356, PCT publication WO 85/01856, and U.S. Pat. No. 4,684,611), plant RNA virus-mediated transformation (as described, for example in EP 0 067 553 and U.S. Pat. No. 4,407,956), liposome-mediated transformation (as described, for example in U.S. Pat. No. 4,536,475), and other methods such as the methods for transforming certain lines of corn (Fromm et al., 1990, Bio/Technology 8, 833-839; Gordon-Kamm et al., 1990, The Plant Cell 2, 603-618, U.S. Pat. No. 5,767,367) and rice (Shimamoto et al., 1989, Nature 338, 274-276; Datta et al., 1990, Bio/Technology 8, 736-740) and the recently described method for transforming monocots generally (PCT publication WO 92/09696).

Different conventional procedures can be followed to obtain combined expression of two ISP proteins in transgenic plants as summarized below:

I. Chimeric gene constructs whereby two ISP DNA sequences and a marker gene are transferred to the plant genome as a single piece of DNA and lead to the insertion in a single locus in the genome.

Ia. The genes can be engineered in different transcriptional units each under control of a distinct promoter.

To express two ISP proteins and a marker protein as separate transcriptional units, several promoter fragments directing expression in plant cells can be used as described above. All combinations of the promoters mentioned above in the chimaeric constructs for one ISP gene are possible. The ISP coding region in each chimeric gene of this invention can be the intact isp gene or preferably an insecticidally-effective part of the intact isp gene. The individual chimeric genes are cloned in the same plasmid vector according to standard procedures (e.g., EP 0 193 259).

Ib. Two genes (e.g., either an isp and a marker gene or two isp genes) or more can be combined in the same transcriptional unit.

To express two isp genes in the same transcriptional unit, the following cases can be distinguished:

In a first case, hybrid genes in which the coding region of one gene is fused in frame with the coding region of another gene can be placed under the control of a single promoter. Fusions can be made between either an isp and a marker gene or between two isp genes.

Also, between each gene encoding an ISP or an insecticidally-effective fragment thereof, a gene fragment encoding a protease (e.g., trypsin, cysteine or serine protease)-sensitive protein part could be included, such as a gene fragment encoding a part of the ISPs which is removed or cleaved upon activation by the midgut enzymes of the target insect species. Alternatively, between each gene encoding an ISP or an insecticidally-effective fragment thereof, a gene fragment can be included encoding a peptide of about 16-20 amino acids which has the capability to mediate cleavage at its own C-terminus by an enzyme-independent reaction (Halpin et al., 1999, Plant J. 17, 453-459, U.S. Pat. No. 5,846,767), or a gene fragment encoding a linker peptide sequence which allows the production of a recombinant cell with significant toxicity to the target insects.

In a second case, the coding regions of the two respective isp genes can be combined in dicistronic units placed under the control of a promoter. The coding regions of the two isp genes are placed after each other with an intergenic sequence of defined length. A single messenger RNA molecule is generated, leading to the translation into two separate gene products. Based on a modified scanning model (Kozak, 1987, Mol. Cell. Biol. 7, 3438-3445), the concept of reinitiation of translation has been accepted provided that a termination codon in frame with the upstream ATG precedes the downstream ATG. Experimental data also demonstrated that the plant translational machinery is able to synthesize several polypeptides from a polycistronic mRNA (Angenon et al., 1989, Mol. Cell. Biol. 9, 5676-5684).

Based on the mechanism of internal initiation of translation (Jackson and Kaminski, 1995, RNA 1, 985-1000) initiation of translation of the second gene occurs by binding of the 43S pre-initiation complex to a specific intergenic sequence (internal ribosome entry sequence; IRES). Experimental data also demonstrated that the plant translational machinery is able to synthesize several polypeptides from a polycistronic mRNA containing intergenic IRES-elements (Hefferon et al., 1997, J Gen Virol 78, 3051-3059; Skulachev at al., 1999, Virology 263, 139-154; PCT patent publication WO 98/54342).

II. A chimeric construct with one isp gene that is transferred to the genome of a plant already transformed with one isp gene:

Several genes can be introduced into a plant cell during sequential transformation steps (retransformation), provided that an alternative system to select transformants is available for the second round of transformation, or provided that the selectable marker gene is excised from the plant genome using DNA recombination technology (e.g., published PCT applications WO 94/17176 and WO 91/09957). This retransformation leads to the combined expression of isp genes which are introduced at multiple loci in the genome. Preferably, two different selectable marker genes are used in the two consecutive transformation steps. The first marker is used for selection of transformed cells in the first transformation, while the second marker is used for selection of transformants in the second round of transformation. Sequential transformation steps using kanamycin and hygromycin have been described, for example by Sandler et al. (1988, Plant Mol. Biol. 11, 301-310) and Delauney et al. (1988, Proc. Natl. Acad. Sci. U.S.A. 85, 4300-4304).

III. Chimeric constructs with isp genes, that are separately transferred to the nuclear genome of separate plants in independent transformation events and are subsequently combined in a single plant genome through crosses.

The first plant should be a plant transformed with a first isp gene or an F1 plant derived thereof through selfing (preferably an F1 plant which is homozygous for the isp gene). The second plant should be a plant transformed with a second isp gene or an F1 plant derived thereof through selfing (preferably an F1 plant which is homozygous for the second isp gene). Selection methods can be applied to the plants obtained from this cross in order to select those plants having the two isp genes present in their genome (e.g., Southern blotting) and expressing the two ISPs (e.g., separate ELISA detection of the immunologically different ISPs). This is a useful strategy to produce hybrid varieties from two parental lines, each transformed with a different isp gene, as well as to produce inbred lines containing two different isp genes through crossing of two independent transformants (or their F1 selfed offspring) from the same inbred line.

IV. Chimeric constructs with one or more isp genes separately transferred to the genome of a single plant in the same transformation experiment leading to the insertion of the respective chimeric genes at the same or at multiple loci.

Cotransformation involves the simultaneous transformation of a plant with two different expression vectors, one containing a first isp gene, the second containing a second isp gene. Along with each isp gene, a different marker gene can be used, and selection can be made with the two markers simultaneously. Alternatively, a single marker can be used, and a sufficiently large number of selected plants can be screened in order to find those plants having the two isp genes (e.g., by Southern blotting) and expressing the two proteins (e.g., by means of ELISA). Cotransformation with more than one T-DNA can be accomplished by using simultaneously two different strains of Agrobacterium, each with a different Ti-plasmid (Depicker et al., 1985, Mol. Gen. Genet. 201, 477-484) or with one strain of Agrobacterium containing two T-DNAs on separate plasmids (de Framond et al., 1986, Mol. Gen. Genet. 202, 125-131). Direct gene transfer, using a mixture of two plasmids or fragments thereof, can also be employed to cotransform plant cells with a selectable and a non-selectable gene (Schocher et al., 1986, Bio/technology 4, 1093-1096).

The resulting transformed plant can be used in a conventional plant breeding scheme to produce more transformed plants with the same characteristics or to introduce the insecticidally effective isp gene in other varieties of the same or related plant species. Seeds, which are obtained from the transformed plants, contain the insecticidally effective isp gene as a stable genomic insert. Cells of the transformed plant can be cultured in a conventional manner to produce the insecticidally effective portion of the ISP protein which can be recovered for use in conventional insecticide compositions against insects. Of course, the above possibilities of combined production of ISP proteins in plants is as well applicable to active fragments of the ISP proteins or the ISP equivalents of this invention. The insecticidally effective isp gene is inserted in a plant cell genome so that the inserted gene is downstream (i.e., 3') of, and operably linked to, a promoter which can direct the expression of the gene part in the plant cell. This is preferably accomplished by inserting the isp chimeric gene in the plant cell genome, particularly in the nuclear or chloroplast genome. Preferred promoters include: the strong constitutive 35S promoters (the "35S promoters") of the cauliflower mosaic virus (CaMV) of isolates CM 1841 (Gardner et al., 1981, Nucl. Acids Res. 9, 2871-2887), CabbB-S (Franck et al., 1980, Cell 21, 285-294) and CabbB-JI (Hull and Howell, 1987, Virology 86, 482-493); promoters from the ubiquitin family (e.g., the maize ubiquitin promoter of Christensen et al., 1992, Plant Mol. Biol. 18, 675-689; see also Cornejo et al., 1993, Plant Mol. Biol. 23, 567-581), the gos2 promoter (de Pater et al., 1992, Plant J. 2, 837-844), the emu promoter (Last et al., 1990, Theor. Appl. Genet. 81, 581-588), rice actin promoters such as the promoter described by Zhang et al. (1991, The Plant Cell 3, 1155-1165); and the TR1' promoter and the TR2' promoter (the "TR1' promoter" and "TR2' promoter", respectively) which drive the expression of the 1' and 2' genes, respectively, of the T-DNA (Velten et al., 1984, EMBO J. 3, 2723-2730). Alternatively, a promoter can be utilized which is not constitutive but rather is specific for one or more tissues or organs of the plant (e.g., leaves and/or roots) whereby the inserted isp gene is expressed only in cells of the specific tissue(s) or organ(s). In a preferred embodiment of the invention, the insecticidally effective isp gene is selectively expressed in the roots of a plant, preferably corn, by placing the insecticidally effective gene part under the control of a root-preferred promoter (i.e., a promoter which is most active in root tissue, preferably a promoter with no or little transcription in non-root tissue such as pollen, leaves and stem, more particularly a promoter only resulting in detectable transcription in root tissue). Root-preferred promoters need not be exclusively active in root tissue. Root-preferred promoters in accordance with this invention include but are not limited to: promoters located immediately upstream of a DNA sequence corresponding to a root-specific cDNA, preferably from corn; the promoter of U.S. Pat. No. 5,837,876, published PCT patent applications WO 00/29594, WO 00/73474, WO 01/00833, or U.S. Pat. No. 6,008,436; the ZRP2 promoter of U.S. Pat. No. 5,633,363 and Held et al. (1997, Plant Mol. Biol. 35, 367-375, Genbank accession number U38790); the promoter of U.S. Pat. No. 5,817,502; the promoter described by de Framond (1991, FEBS 290: 103-106; EP 0 452 269), the root-specific promoter of the peroxidase gene PDX1 from wheat (Hertig et al., 1991, Plant Molec. Biol. 16, 171-174), the promoter of U.S. Pat. No. 5,837,848, the promoter of PCT publication WO 015662, the promoter of Goddemeier et al. (1998, Plant Mol. Biol. 36, 799-802). Other root-specific or root-preferred promoters which may be useful in this invention include the promoters described by Hirel et al., 1992, Plant Mol. Biol. 20, 207; Keller and Baumgartner, 1991, The Plant Cell 3, 1051-1061; Sanger et al., 1990, Plant Mol. Biol. 14, 433-443; Miao et al., 1991, The Plant Cell 3, 11-22; Bogusz et al., 1990, The Plant Cell, 2, 633-641; Leach and Aoyagi, 1991, Plant Science 79, 69-76; Teeri et al., 1989, EMBO Journal 8, 343-350, all of which are incorporated herein by reference.

Expression in leaves of a plant can be achieved by using the promoter of the ribulose-1,5-bisphosphate carboxylase small subunit gene of the plant itself or of another plant such as pea as disclosed in U.S. Pat. No. 5,254,799. Another alternative is to use a promoter whose expression is inducible (e.g., by temperature or chemical factors). Also, for corn plants, particularly at the time adult corn rootworms are present in corn rootworm fields, expression in pollen is preferred, by using promoter regions resulting in expression in corn pollen, e.g. the promoters described in published PCT applications WO 93/25695 and WO 01/12799.

The insecticidally effective isp gene is inserted in the plant genome so that the inserted gene part is upstream (i.e., 5') of suitable 3' end transcription regulation signals (i.e., transcript formation and polyadenylation signals).

This is preferably accomplished by inserting the isp chimeric gene in the plant cell genome. The choice of the 3' regulatory sequence in the chimeric gene of the invention is not critical. In some cases good expression can be obtained when no such region is present in the chimeric gene, since a DNA sequence at the insertion site can act as a 3' regulatory sequence. Preferred polyadenylation and transcript formation signals include those of the CaMV 35S (Mogen et al., 1990, The Plant Cell 2, 1261-1272), the octopine synthase gene (Gielen et al., 1984, EMBO J. 3, 835-845), the nopaline synthase gene (Depicker et al., 1982, J. Mol. Appl. Genet. 1, p. 561), and the T-DNA gene 7 (Velten and Schell, 1985, Nucleic Acids Research 13, 6981-6998), which act as 3'-untranslated DNA sequences in transformed plant cells.

The insecticidally effective isp gene can optionally be inserted in the plant genome as a hybrid gene (U.S. Pat. No. 5,254,799; Vaeck et al., 1987, Nature 327, 33-37) under the control of the same promoter as a selectable marker gene, such as the neo gene (EP 0 242 236) encoding kanamycin resistance, so that the plant expresses a fusion protein.

All or part of the isp gene, can also be used to transform other bacteria, such as a *B. thuringiensis* strain which has insecticidal activity against *Lepidoptera* or Coleoptera, or root-colonizing bacteria, e.g. root-colonizing *Pseudomonas putida* (Vilchez et al., J. Bacteriol. 182, 91-99). Thereby, a transformed bacterial strain can be produced which is useful for combatting insects and which can affect a wide spectrum of lepidopteran and coleopteran insect pests. Transformation of bacteria, such as bacteria of the genus *Agrobacterium*, *Bacillus* or *Escherichia*, with all or part of the isp gene of this invention or its equivalent, incorporated in a suitable cloning vehicle, can be carried out in a conventional manner, such as heat shock transformation (Bergmans et al., 1981, J. Bacteriol 146, 564-570) or conventional electroporation techniques as described in Mahillon et al. (1989, FEMS Microbiol. Letters 60, 205-210) and in PCT Patent publication WO 90/06999.

Transformed bacterial strains, such as *Bacillus* species strains, preferably *Bacillus thuringiensis* strains, containing the isp gene of this invention can be fermented by conventional methods (Dulmage, 1981, "Production of Bacteria for Biological Control of Insects" in Biological Control in Crop Production, Ed. Paparizas, D. C., Osmun Publishers, Totowa, N. J., USA, pp. 129-141; Bernhard and Utz, 1993, "Production of *Bacillus thuringiensis* insecticides for experimental and commercial uses", In *Bacillus thuringiensis*, An Environmental Biopesticide: Theory and Practice, pp. 255-267, eds. Entwistle, P. F., Cory, J. S., Bailey, M. J. and Higgs, S., John Wiley and Sons, New York) to provide high yields of cells.

An insecticidal, particularly anti-coleopteran, preferably anti-corn rootworm composition of this invention can be formulated in a conventional manner using the microorganisms transformed with the isp gene, or preferably their respective ISP proteins or insecticidally effective portions thereof as an active ingredient, together with suitable carriers, diluents, emulsifiers and/or dispersants (e.g., as described by Bernhard and Utz, 1993, supra). This insecticide composition can be formulated as a wettable powder, pellets, granules or dust or as a liquid formulation with aqueous or non-aqueous solvents as a foam, gel, suspension, concentrate, etc. Known microorganisms include cells of *Pseudomonas* or other bacteria which serve to encapsulate the proteins in a stable environment prior to application to the insects. Also included in the invention is a product comprising the ISP1A and ISP2A protein of the invention as a combined preparation for simultaneous, separate or sequential use to protect corn plants against corn rootworms, particularly such product is an insecticidal composition or a transgenic corn plant.

A method for controlling insects, particularly Coleoptera, in accordance with this invention can comprise applying (e.g., spraying), to a locus (area) to be protected, an insecticidal amount of the ISP proteins or host cells transformed with the isp gene of this invention. The locus to be protected can include, for example, the habitat of the insect pests or growing vegetation or an area where vegetation is to be grown.

To obtain the ISP protein, cells of the recombinant hosts expressing the ISP protein can be grown in a conventional manner on a suitable culture medium and the protein can then be obtained from the medium using conventional means. The ISP protein can then be separated and purified by standard techniques such as chromatography, extraction, electrophoresis, or the like. The protease-resistant toxin form can then be obtained by protease, e.g. cysteine or serine protease, digestion of the protein.

Bio-assays for testing the insecticidal efficacy are well known in the art. A method for corn rootworm testing is described in Marrone et al. (1985, J. Econ. Entomol. 78, 290-293), but many other methods are available to test insects on artificial diet or on transgenic plants, e.g. U.S. Pat. No. 5,990,383. In a suitable bio-assay the proper controls are included to check for background mortality.

The following Examples illustrate the invention, and are not provided to limit the invention or the protection sought. Many variants or equivalents of these Examples can be made or designed by a person of ordinary skill in the art without departing from the teachings of the invention and the common knowledge. The sequence listing referred to in this application (which forms part of this application and is attached thereto), is as follows:

Sequence Listing:
SEQ ID NO: 1—amino acid and DNA sequence of ISP1A protein and DNA
SEQ ID NO: 2—amino acid sequence of ISP1A protein.
SEQ ID NO: 3—amino acid and DNA sequence of ISP2A protein and DNA.
SEQ ID NO: 4—amino acid sequence ISP2A protein.
SEQ ID NO: 5—DNA sequence of the short zrp2 promoter fragment (n=any nucleotide)
SEQ ID NO: 6—DNA sequence of the long zrp2 promoter fragment (n=any nucleotide)
SEQ ID NO: 7—DNA sequence encoding ISP2A-1 protein
SEQ ID NO: 8—amino acid sequence of ISP2A-1 protein
SEQ ID NO: 9—DNA sequence encoding ISP1A-1 protein fragment
SEQ ID NO: 10—amino acid sequence of ISP1A-1 protein Unless otherwise stated in the Examples, all procedures for making and manipulating recombinant DNA are carried out by the standard procedures described in Sambrook et al., Molecular Cloning—A Laboratory Manual, Second Ed., Cold Spring Harbor Laboratory Press, NY (1989), and in Volumes 1 and 2 of Ausubel et al. (1994) Current Protocols in Molecular Biology, Current Protocols, USA. Standard materials and methods for plant molecular biology work are described in Plant Molecular Biology Labfax (1993) by R. R. D. Croy, jointly published by BIOS Scientific Publications Ltd (UK) and Blackwell Scientific Publications (UK). Procedures for PCR technology can be found in "PCR protocols: a guide to methods and applications", Edited by M. A. Innis, D. H. Gelfand, J. J. Sninsky and T. J. is White (Academic Press, Inc., 1990).

EXAMPLES

Example 1

Characterization of the IB120-A Strain

A bacterial strain, named herein the IB120-A strain, was found in a field in the state of Morelos, Mexico.

The strain was grown overnight on LB agar plates (LB medium with 1.5% agar added; LB medium: 10 g/l trypton, 10 g/l NaCl, 5 g/l yeast extract, pH 7.3) at 28° C. For small scale cultures, 20 ml TB medium (Terrific Broth: 12 g/l tryptone, 24 g/l yeast extract, 3.8 g/l $KH_2PO_4$, 12.5 g/l $K_2HPO_4$, 5 ml/l glycerol, pH 7.1) was inoculated and grown for 65 hours at 28° C. on a rotating platform having about 70 rotations per minute. After 65 hours, a protease inhibitor mixture was added to the culture. This cocktail has the following ingredients (volumes given are those required to add to one 20 ml culture): 200 µl PMSF (100 mM), 200 µl of a mixture of benzamidine.HCl (100 mM) and epsilon-amino-n-caproic acid (500 mM), 400 µl EGTA (0.5M), 40 µl antipain (0.5 mg/ml)/leupeptin (0.5 mg/ml) and 20 µl beta-mercapto ethanol (14M). The culture medium to which the protease inhibitor mixture had been added, was then centrifuged for 20 minutes at 3000 rpm. In some cases, the supernatant was concentrated about 4 times using Centriprep YM-10 Centrifugal Filter Devices (Millipore Cat. No. 4305). For long term storage, a loop of sporulated cells was added to 0.5 ml of 25% or 50% glycerol and after vortexing, stored at −70° C. Sporulated cells were obtained by growth of the strain on LB agar plates until sporulation (as apparent under the light microscope).

After cultivating on LB agar plates of single cell colonies, microscopical analysis of the IB120-A strain culture showed the presence of rod-shaped motile single vegetative cells and swollen sporangia containing an ovale spore. No parasporal crystals were detected in cultures of the IB120-A strain.

Supernatant of the IB120-A strain showed strong toxicity to *Diabrotica virgifera* larvae (hereinafter termed "Dv") in surface contamination assays on artificial diet (diet as described by Sutter et al. (1971, J. Econ. Entomol. 64, 65-67)). The assays were done at 24° C. (+/−1° C.) in 24 multiwell Costar plates at 50 microliter toxin solution per well (2 $cm^2$), 6 wells were analyzed with 4 L1 (first instar) larvae per well for each sample (scoring after 7 days).

Screening of supernatant harvested at 7, 24, 30, 48 and 120 hours after initiation of the culture showed the strongest toxicity to Dv at 48 hours, with no significant toxicity found at 7 hours. At 48 hours, mortality in the 50-60% range was still found when the supernatant (at total protein concentration of 214 microgr/ml) was diluted at 1/1024.

Loss of activity of IB120-A supernatant harvested 48, 65 and 144 hours after culture initiation (in dilutions of 1/1 to 1/8) upon heat treatment and retention of activity after ammonium sulphate precipitation indicated that the toxic compound is likely a protein.

Preliminary characterization of the IB120-A strain by PCR primers for gyrase B genes (Yamada et al., 1999, Appl. Environm. Microbiol. 65, 1483-1490) suggested that it was not a *Bacillus* strain of the subspecies *thuringiensis*, *anthracis* or *cereus*. Also, no amplification products were obtained using PCR primers specifically characterizing the 16S RNA sequences of the genus *Paenibacillus* which are also recognizing the species *Bacillus lentimorbus* and *Bacillus popilliae* (Pettersson et al., 1999, Int J Syst Bacteriol. 49(2), 531-540). Growth in NB (nutrient broth: 3 g/l bacto beef extract, 5 g/l bacto peptone, pH 6.8) medium indicated that the new strain was not a *Bacillus larvae* species. Thus, this IB120-A strain seems to be different from previously isolated *Bacillus* strains known to produce secreted insecticidal proteins which are not contained in crystals.

Based on the rod-like shape and the aerobic growth, the strain could be a *Bacillus* species strain. With a set of general and specific primers for cry3 *Bacillus thuringiensis* genes, no amplification products were found when analyzing strain IB120-A.

Detailed analysis of the IB 120-A strain using standard microbial identification techniques, including fatty acid analysis and API 50CHB tests combined with API 20E tests, showed that this strain is a *Brevibacillus laterosporus* species strain.

Example 2

Isolation and Characterization of isp1 and isp2 DNAs/Proteins

In order to isolate the genes responsible for the toxicity of IB120-A, total DNA from this strain was prepared and partially digested with Sau3A. The digested DNA was size fractionated on a sucrose gradient and fragments ranging from 7 kb to 10 kb were ligated to the BamH1-digested and TsAP (thermosensitive alkaline phosphatase)—treated cloning vector pUC19 (Yannisch-Perron et al, 1985, Gene 33, 103-119.). The ligation mixture was electroporated in *E. coli* XL1-Blue cells. Transformants were plated on LB-triacillin plates containing Xgal and IPTG and white colonies were selected to be used in filter hybridization experiments. Recombinant *E. coli* clones containing the vector were then screened with a Digoxigenine ("DIG") labeled probe which was prepared as follow. First, a PCR was performed using as template cells from strain IB120-A. The resulting amplification product was gel-purified and used as template in a secondary PCR reaction using DIG-labeled dNTPs and the same primers as in the first PCR reaction. An appropriate amount of this amplification product was used in hybridization reactions.

Following the identification of a positive colony containing a plasmid harboring the full length isp genes, the sequence of these genes was determined using the dye terminator labeling method and a Perkin Elmer ABI Prism-377 DNA sequencer. The sequences of the 2 open reading frames found in the cloned DNA fragment of a positive colony are shown in SEQ ID NO: 1 and 3. These DNA sequences were found to be organized in an operon and encode novel proteins, ISP1A (SEQ ID NO: 2) and ISP2A (SEQ ID NO: 4) which have been found to be the causal agents of the high insecticidal activity observed. A positive colony containing the pUC-derived plasmid with the genes responsible for toxicity (in plasmid pUCIB120/ISP) has been deposited under the provisions of the Budapest treaty in *E. coli* XL1 Blue as LMBP 4009 on Jan. 11, 2000.

A plasmid preparation was made from the positive colony and this plasmid was cut using XbaI and EcoRI (resulting in an about 7 Kb fragment) and ligated in the shuttle vector pSL40 which had been cut using the same restriction enzymes. This yielded plasmid pSLIB120/ISP. The plasmid pSLIB120/ISP was then transferred into a crystal—minus *B. thuringiensis* strain. Supernatant from this recombinant Bt strain was obtained as follows.

The strain was grown overnight on LB agar plates containing erythromycin (20 μg/ml) at 28° C. For small scale cultures, 20 ml TB medium containing erythromycin (20 μg/ml) was inoculated and grown for 65 hours at 28° C. on a rotating platform having about 70 rotations per minute. After 65 hours, a protease inhibitor mixture was added to the culture. This cocktail has the following ingredients (volumes given are those required to add to one 20 ml culture): 2000 PMSF (100 mM), 2000 of a mixture of benzamidine.HCl (100 mM)/epsilon-amino-n-caproic acid (500 mM), 4000 EGTA (0.5M), 400 antipain (0.5 mg/ml)/leupeptin (0.5 mg/ml) and 200 beta-mercapto ethanol (14M). The culture medium to which the protease inhibitor mixture had been added, was then centrifuged for 20 minutes at 3000 rpm. In some cases, the supernatant was concentrated about 4 times using centriprep YM-10 Centrifugal Filter Devices (Millipore, Cat. No. 4305).

Insecticidal activity of the supernatant at 48 hours after culture initiation of the recombinant Bt strain containing the pSLIB120/ISP plasmid using the Dv surface contamination assay described above, showed that the supernatant still had significant mortality in the 60% range at a 1/1024 dilution, while control mortality (the controls included supernatant of the untransformed Bt strain) was 0%. This shows that the isolated DNA encodes an insecticidal ingredient of the IB120-A strain, and upon transfer to another bacterium is also expressed and secreted in the culture medium. Analysis of toxicity of another independent Bt-crystal-minus strain transformed with the pSLIB120/ISP plasmid confirmed the high insecticidal activity of the supernatants compared to that of the untransformed control.

The LC50 value of the supernatant of the Bt strain expressing the two ISP proteins was found to be 3.5 ng/cm$^2$ after 4 days using the above-described surface contamination assay with Dv larvae (based on total supernatant protein concentration). Detailed analysis of the toxicity of supernatant produced by the recombinant Bt strain expressing the ISP1A and ISP2A proteins to selected coleopteran insects is reported in Table 1 below. The ISP proteins of the invention were found to have significant insecticidal activity to Western, Northern and Southern corn rootworm larvae, and also to larvae of the Colorado potato beetle and the cotton boll weevil.

The mature ISP1 and ISP2 proteins were purified to apparent homogeneity by ammonium sulphate precipitation followed by passage over different chromatographical columns. The chromatographical analysis suggest that the ISP1A and ISP2A proteins are present in the supernatant in equimolar ratio. The ISP1A protein was found to be of rather hydrophobic nature, while ISP2A was of rather hydrophilic nature. Amino-terminal sequence determination of the mature ISP1A and ISP2A proteins produced in the recombinant crystal-minus Bt strain showed that amino acid position 38 in SEQ ID NO: 2 for ISP1A and amino acid position 51 in SEQ ID NO: 4 for ISP2A are the N-terminal amino acids of the active proteins present in supernatant of such transformed Bt strain. The N-terminus for ISP1A was found to be IATTTQASKD, that for ISP2A was found to be LVKTT-NNTED, which matches fully with the amino acid sequence of the DNA sequences isolated.

The apparent molecular weight of the pure mature ISP1A protein was determined to be about 100 kD in 8% SDS-PAGE gel electrophoresis, that of the pure mature ISP2A protein was determined to be about 45 kD protein in 10% SDS-PAGE gel electrophoresis, using molecular weight markers of 37, 50, 75, 100, and 150 kD.

The activity of the mature ISP1A and ISP2A proteins as produced by the recombinant strain was evaluated against several insects. The results against selected coleopteran insects are shown in Table 1 below.

TABLE 1

| Coleopteran activity of ISP1A-ISP2A: | | | |
| --- | --- | --- | --- |
| Insect | Stage | LC50 (μg/ml) (95% CL) | LC90 (μg/ml) (95% CL) |
| Dv | L1 | 0.437 (0.321-0.563) | 1.689 (1.250-2.597) |
|  | L2 | 3.84 (—) | 117.4 (—) |
|  | L3 | 21.674* (5.012-100.432) | 531.76 (110.688-86864) |
| Db | L1 | 0.213 (0.116-0.338) | 0.890 (0.542-2.006) |
| Du | L1 | 4.91 (1.65-13.26) | 30.06 (11.52-329.72) |

TABLE 1-continued

Coleopteran activity of ISP1A-ISP2A:

| Insect | Stage | LC50 (μg/ml) (95% CL) | LC90 (μg/ml) (95% CL) |
|---|---|---|---|
| Ld | L1 + 2d | 0.037 (—) | 1.068 (—) |
| Ag | L1 | 207.1 (84.3-654.7) | 8759.2 (1865.8-620175.8) |

Legend to Table 1:
Dv: *Diabrotica virgifera*, Western corn rootworm;
Db: *Diabrotica barberi*, Northern corn rootworm;
Du: *Diabrotica undecimpunctata howardi*, Southern corn rootworm;
Ld: *Leptinotarsa decemlineata*, Colorado potato beetle;
Ag: *Anthonomus grandis*, cotton boll weevil;
L1: first larval stage;
L2: second larval stage;
L3: third larval stage;
L1 + 2d: 2d after egg hatch;
*90% CL (CL = Confidence Limits, LC50: total supernatant protein concentration when 50% of the insects are killed).
Bioassays used:
Dv, Db, Du: surface contamination assay on artificial diet (see above for description) at ratio of 25 μl/cm², scoring after 7 days;
Ld: diptest with potato foliage (cut potato foliage dipped in toxin solution, allowed to dry and put in a petri dish (9 cm diam.) with 10 larvae; after 1 day untreated foliage was added to the petridish, scoring was after 5 days);
Ag: artificial diet incorporation test: diet as described by Moore and Whisnant, Handbook of Insect Rearing, Vol. I, Pritah Singh and R. F. Moore; Elsevier, Amsterdam, 1985, p. 217; assay: incorporation of 2 ml toxin solution per 25 ml diet, in 24 multiwell Costar plates (about 1 ml/well), 1 egg per well, 20 wells per sample, scoring after 14 days).

In the assays reported in Table 1, controls (untreated food, food supplied with supernatant of a non-transformed Bt-crystal-minus strain or with water) did not show any mortality above 20% for any of the above insects (a variation from 5 to 20% control mortality was found according to larval stage and insect species (the 20% value is for the third larval stage of Dv)).

The LC50 values obtained for *Diabrotica virgifera* larvae using the bio-assay as described above, when an equimolar combination of ISP1A and ISP2A protein was applied after purification of these proteins from the supernatans of the recombinant Bt strain, were not significantly different from those obtained above.

Bio-assays of a mixture of the mature ISP1A and ISP2A protein in standard surface contamination assays against selected lepidopteran insects (*Ostrinia nubilialis, Heliothis virescens, Helicoverpa zea, Spodoptera frugiperda, Sesamia nonagrioides, Spodoptera littoralis, Helicoverpa armigera,* and *Manduca sexta*) showed that the ISP proteins of this invention do not cause any mortality in these insects above control levels. This evidences the coleopteran-specific nature of the proteins of this invention. Preliminary bio-assays with two aphid species also showed that a mixture of the ISP1A and ISP2A proteins did not cause any significant mortality in these insects.

To determine which fragment of the isp genes are sufficient to encode an ISP protein complex toxic to *Diabrotica* larvae, a series of C-terminally truncated ISP proteins were made by inserting a stopcodon in the ORF of the isp genes at different positions (and thus making different 3' gene truncations). The stopcodons were inserted at random positions using the Genome Priming System (GPS, New England Biolabs, catalog #7100). Using this system, a 1.7 kb transposon (containing stopcodons in all three reading frames and 2 sequences complementary to specific primers) is inserted randomly but only once in the 'target' DNA. The position of the insertion, and therefore, the truncation can then be estimated by PCR screening using a gene-specific primer and a transposon-specific primer or can be precisely determined by sequencing. A set of constructs with a transposon at different positions in one of the isp genes was then transformed individually in a crystal minus Bt strain and the susceptibility of Western corn rootworm larvae to the supernatant of each recombinant Bt strain was tested using the assay described above.

For truncation of the isp2 gene, a fragment containing the gene was cut out of pSLIB120/ISP using BstBI and PmII. Following the GPS reaction, this fragment was then ligated into the pSLIB120/ISP vector, cut with the same enzymes. Recombinant *E. coli* colonies were PCR-screened in order to estimate the position of the transposon insertion site. A set of 10 clones with the transposon at different positions in the second half (3' half) of the isp2 gene was selected. Plasmid DNA of these clones was transformed in a dcm and dam methylase negative *E. coli* strain GM2163. Plasmid DNA isolated from this strain was then transformed in a crystal-minus Bt strain. Supernatant was prepared and bioassayed, using supernatant from the Bt strain transformed with pSLIB120/ISP as a positive control and supernatant from the crystal-minus Bt strain as a negative control. For truncation of the isp1 gene, a fragment was cut out of pSLIB120/ISP using PmII and EcoRI. The same methodology was followed as for the truncation of the isp2 gene.

The results of the transposon insertion analysis indicate that truncation of relatively large segments of the isp2A gene at the 3' end abolishes toxicity, indicating that no or only a relatively short C-terminal truncation is allowed in the ISP2A protein. After sequencing, the smallest C-terminally truncated ISP2A toxin fragment retaining toxicity in this study when tested in combination with the ISP1A protein was found to end at amino acid position 449 in SEQ ID NO: 4.

The results of these analyses indicate that a larger truncation of the ISP1A protein at the 3' end is possible: sequence determination showed that the toxic fragment with the largest C-terminal truncation ended at amino acid position 768 in SEQ ID NO: 2. Thus, approximately 300 by of the ISP1A coding region can be deleted at the 3' side without losing toxicity.

The above study also indicates that insecticidal activity is reduced to the background level when no functional ISP1A is produced, confirming the binary nature of the ISP proteins of this invention.

The ISP2A protein from amino acid position 51 to amino acid position 449 in SEQ ID NO: 4 and the ISP1A protein from amino acid position 38 to amino acid position 768 in SEQ ID NO: 2 are thus useful insecticidal fragments of the ISP proteins.

Furthermore, a chimeric gene containing a DNA fusion of the ISP1A and ISP2A genes was expressed in a crystal-minus *Bacillus thuringiensis* berliner 1715 strain. A DNA sequence encoding an Arg-Lys-linker (RKRKRK) (SEQ ID NO: 11) or a DNA sequence encoding a Gly-linker (GGGGGG) (SEQ ID NO 12) was provided between the open reading frames encoding the ISP2A and the ISP1A proteins (ISP2A still has its N-terminal signal peptide present, while ISP1A lacks its signal peptide), so that a translational fusion protein is produced; i.e. a fusion protein in which the speficied linker connects the ISP2A protein (as the N-terminal fusion partner) to the ISP1A protein (as the C-terminal fusion partner). The recombinant Bt strain proved to cause mortality to *Diabrotica virgifera* which was significantly higher then that of the untransformed control strain (i.e., the crystal-minus Bt 1715 strain). This shows the possibility of producing the ISP proteins of the invention as a fusion protein in a recombinant host cell by using a single chimeric gene. Obviously, as explained in the description of the invention, multiple different approaches can be used to achieve the production of a fusion protein in the recombinant cell, e.g. cells of a plant.

Example 3

Production of ISP Proteins in Plants

To obtain optimal expression in plants, the isp1A and isp2A native DNA sequences are modified to produce modified DNA sequences encoding the ISP1A and ISP2A proteins. The optimized DNA sequences encoding the ISP1A-1 and ISP2A-1 proteins with their signal peptides replaced by a methionine and alanine amino acid are shown in SEQ ID NO: 9 and 7, respectively.

These coding regions are inserted in a chimeric gene operably linked to suitable regulatory sequences, e.g., a promoter based on the short or long zrp2 promoter sequences of SEQ ID NO: 5 or 6 using standard techniques, and appropriate 3' transcription termination and polyadenylation sequences. In some constructs, the above chimeric genes contain a DNA sequence encoding the optimized chloroplast transit peptide (in place of the N-terminal bacterial signal peptide) as described in U.S. Pat. No. 5,510,471 (or Reissued US Patent RE 036449) resulting in targeting to the plastids or a signal peptide causing targeting to the cell wall. Other signal peptides effective in plant cells can similarly be used, preferably the signal peptide encoded by the alpha-amylase 3 gene of rice (Sutliff et al., 1991, Plant Molec. Biol. 16, 579-591), the signal peptide encoded by the ferredoxin NADP+ oxidoreductase gene from spinach (Oelmueller et al., 1993, Mol. Gen. Genet. 237, 261-272), or the signal peptide encoded by the proteinase inhibitor II gene of potato (Keil et al., 1986, Nucl. Acids Res. 14, 5641-5650).

Corn cells are stably transformed with the above isp1A and isp2A chimeric genes using *Agrobacterium*-mediated transformation (Ishida et al., 1996, Nature Biotechnology 14, 745-750; and U.S. Pat. No. 5,591,616), protoplast transformation as described in U.S. Pat. No. 5,792,936, or by electroporation using wounded and enzyme-degraded embryogenic callus, as described in WO 92/09696 or U.S. Pat. No. 5,641,664 (all of these above references are incorporated herein by reference). Corn plants are regenerated from the transformed cells and are selected for optimal expression levels in roots and for adequate overall agronomic characteristics. The thus obtained transgenic corn plants producing the above ISP proteins of the invention cause significant mortality to *Diabrotica virgifera* larvae attempting to feed on such plants.

In accordance with this invention, stably transformed corn plants are also obtained containing several DNA constructs, so that the corn plant can express one or both the ISP proteins of the invention in its cells under control of the suitable regulatory control regions, together with an appropriate marker gene, preferably a herbicide resistance gene. In these DNA constructs, a preferred 3' transcription termination and polyadenylation sequence is a 215 by fragment containing the 3' transcription termination and polyadenylation sequences obtained from Cauliflower Mosaic virus (Oka et al., 1981, J. Mol. Biol. 147, 217-226). In some constructs, a 5' untranslated leader sequence can be added, preferably those chosen from the leader sequences of a cab22 gene from Petunia (Harpster et al., 1988, Mol. Gen. Genetics 212, 182-190) or the zrp2 gene (Held et al, 1997, Plant Molecular Biology 35, 367-375, Genbank accession number U38790). Preferred promoters in the constructs are promoter-effective parts of the 35S promoter (e.g., Odell et al., 1985, Nature 313, 810-812) or zrp2 promoters (Held et al, 1997, Plant Molecular Biology 35, 367-375, Genbank accession number U38790). The constructs can also contain a signal peptide effective in plant cells besides the above optimized chloroplast transit peptide, namely the transit peptide of the alpha-amylase 3 gene of rice (Sutliff et al., 1991, Plant Molec. Biol. 16, 579-591), the transit peptide of the ferredoxin NADP+ oxidoreductase from spinach (Oelmueller et al., 1993, Mol. Gen. Genet. 237, 261-272), or the transit peptide from the proteinase inhibitor II of potato (Keil et al., 1986, Nucl. Acids Res. 14, 5641-5650). Transformations of plants with the ISPA chimeric genes using a selection from the above preferred elements using techniques available to the person of ordinary skill in the art can be used to achieve the desired goal of the invention.

Preferably the plants also contain a gene encoding a protein conferring resistance to glufosinate or glyphosate, for which a different promoter and/or leader sequence is used, e.g. the gos2 promoter and/or the gos2 leader (de Pater et al., 1992, Plant J. 2, 837-844).

Needless to say, this invention is not limited to the above corn plants, transformation methods nor to the particular ISP proteins or DNA sequences used. Rather, the invention also includes any variant or equivalent of the ISP protein retaining insecticidal activity, such as a protein having substantially the amino acid sequence of the ISP proteins of the invention and having substantially the insecticidal activity of the ISP proteins. Also, any plant which is susceptible to damage by coleopteran insects, particularly corn rootworms, weevils or potato beetles, especially *Diabrotica virgifera* or *Leptinotarsa decemlineata*, preferably an insect selected from the group consisting of: *Agelastica alni, Hypera postica, Hypera brunneipennis, Haltica tombacina, Anthonomus grandis, Tenebrio molitor, Triboleum castaneum, Dicladispa armigera, Trichispa serica, Oulema oryzae, Colaspis brunnea, Lissorhorptrus oryzophilus, Phyllotreta cruciferae, Phyllotreta striolata, Psylliodes punctulata, Entomoscelis americana, Meligethes aeneus, Ceutorynchus* sp., *Psylliodes chrysocephala, Phyllotreta undulate, Leptinotarsa decemlineata, Diabrotica undecimpunctata undecimpunctata, Diabrotica undecimpunctata howardi, Diabrotica barberi* and *Diabrotica virgifera*, is included in the invention as a preferred target for transformation with a DNA encoding an ISP protein.

The invention claimed is:

1. An isolated DNA encoding a protein comprising the amino acid sequence of SEQ ID NO:4 from amino acid residue 51 to amino acid residue 449 or 457; wherein said protein is insecticidal to *Diabrotica virgifera* larvae when ingested by said insect in combination with the protein fragment of SEQ ID NO:2 from amino acid residue 38 to amino acid residue 871.

2. An isolated DNA encoding a protein comprising an amino acid sequence with at least 97% sequence identity to the amino acid sequence of SEQ ID NO:4 or encoding a protein comprising the amino acid sequence of SEQ ID NO: 8; wherein said protein is insecticidal to *Diabrotica virgifera* larvae when ingested by said insect in combination with the protein fragment of SEQ ID NO:2 from amino acid residue 38 to amino acid residue 871.

3. The DNA of claim 1 or 2, comprising an artificial DNA sequence having a different codon usage compared to the naturally occurring DNA sequence of SEQ ID NO:3.

4. A chimeric gene comprising the DNA of claim 3 operably linked to a plant-expressible promoter.

5. The chimeric gene of claim 4, wherein said promoter region is preferentially active in root tissue.

6. The chimeric gene of claim 4 wherein said chimeric gene further comprises a signal peptide for secretion from the cell or for targeting to a cellular organelle.

7. The chimeric gene of claim 6 wherein said signal peptide is a chloroplast transit peptide.

8. A chimeric gene comprising the DNA of claim 1 or 2 operably linked to a plant-expressible promoter.

9. The chimeric gene of claim 8, wherein said promoter region is preferentially active in root tissue.

10. The chimeric gene of claim 8 wherein said chimeric gene further comprises a signal peptide for secretion from the cell or for targeting to a cellular organelle.

11. The chimeric gene of claim 10 wherein said signal peptide is a chloroplast transit peptide.

* * * * *

SEQUENCE LISTING

```
<160> NUMBER OF SEQ ID NOS: 12

<210> SEQ ID NO 1
<211> LENGTH: 2616
<212> TYPE: DNA
<213> ORGANISM: Brevibacillus laterosporus
<220> FEATURE:
<221> NAME/KEY: CDS
<222> LOCATION: (1)..(2613)
```

```
<400> SEQUENCE: 1 atg aaa tat atg aaa aaa gga tta tct agt gtt gta ata ggt acg ttg      48
Met Lys Tyr Met Lys Lys Gly Leu Ser Ser Val Val Ile Gly Thr Leu
1               5                   10                  15 ttc gct tct atg ttt ttg aat ggg aat gta aat gct gtt tac gcg aac      96
Phe Ala Ser Met Phe Leu Asn Gly Asn Val Asn Ala Val Tyr Ala Asn
            20                  25                  30 agt aaa aca aat cag att gct aca aca act cag gca agc aaa gac aac     144
Ser Lys Thr Asn Gln Ile Ala Thr Thr Thr Gln Ala Ser Lys Asp Asn
        35                  40                  45 caa ata gat cga gaa gga cta ctt ggt tat tac ttt aaa gga aaa gat     192
Gln Ile Asp Arg Glu Gly Leu Leu Gly Tyr Tyr Phe Lys Gly Lys Asp
    50                  55                  60 ttt aat gat ctt acc ttg ttt gca ccg aca cgt gat aat act ctt att     240
Phe Asn Asp Leu Thr Leu Phe Ala Pro Thr Arg Asp Asn Thr Leu Ile
65                  70                  75                  80 tat gac caa caa aca gca aat aca cta gta gat caa aag cat caa gaa     288
Tyr Asp Gln Gln Thr Ala Asn Thr Leu Val Asp Gln Lys His Gln Glu
                85                  90                  95 tat cat tct att cgc tgg att gga ttg att cag agt agt gca aca gga     336
Tyr His Ser Ile Arg Trp Ile Gly Leu Ile Gln Ser Ser Ala Thr Gly
            100                 105                 110 gat ttc aca ttt aaa ttg tca gat gat gaa aat gcc atc att gaa ttg     384
Asp Phe Thr Phe Lys Leu Ser Asp Asp Glu Asn Ala Ile Ile Glu Leu
        115                 120                 125 gat ggg aaa gtt att tct gaa aaa ggt aac aat aaa caa agt gtt cat     432
Asp Gly Lys Val Ile Ser Glu Lys Gly Asn Asn Lys Gln Ser Val His
    130                 135                 140 tta gaa aaa gga cag ttg gtg caa ata aaa att gag tac caa tca gac     480
Leu Glu Lys Gly Gln Leu Val Gln Ile Lys Ile Glu Tyr Gln Ser Asp
145                 150                 155                 160 gat gca tta cat ata gat aat aaa att ttt aaa gag ctt aag cta ttc     528
Asp Ala Leu His Ile Asp Asn Lys Ile Phe Lys Glu Leu Lys Leu Phe
                165                 170                 175 aag ata gat agt caa aat cac tct caa caa gtt caa caa gat gaa ctg     576
Lys Ile Asp Ser Gln Asn His Ser Gln Gln Val Gln Gln Asp Glu Leu
            180                 185                 190 aga aac cct gag ttt aat aag aaa gaa acg caa gta ttc tta aag aaa     624
Arg Asn Pro Glu Phe Asn Lys Lys Glu Thr Gln Val Phe Leu Lys Lys
        195                 200                 205 gca tcg aaa aca aat ctt ttt aca caa aaa aca aaa aga gac att gat     672
Ala Ser Lys Thr Asn Leu Phe Thr Gln Lys Thr Lys Arg Asp Ile Asp
    210                 215                 220 gaa gat acg gat aca gat gga gat tct atc cct gat gtt tgg gaa gaa     720
Glu Asp Thr Asp Thr Asp Gly Asp Ser Ile Pro Asp Val Trp Glu Glu
225                 230                 235                 240 aac ggg tat acc att caa aac aaa gtc gca gtc aaa tgg gat gat tcg     768
Asn Gly Tyr Thr Ile Gln Asn Lys Val Ala Val Lys Trp Asp Asp Ser
                245                 250                 255 tta gca agt aaa ggg tat caa aaa ttt act tct aat cca cta gaa gca     816
Leu Ala Ser Lys Gly Tyr Gln Lys Phe Thr Ser Asn Pro Leu Glu Ala
            260                 265                 270 cac aca gtt gga gat ccc tat agt gat tat gaa aaa gct gca aga gat     864
His Thr Val Gly Asp Pro Tyr Ser Asp Tyr Glu Lys Ala Ala Arg Asp
        275                 280                 285 atg ccc tta tcg aat gca aaa gaa act ttt aat cct ctg gtt gcc gcc     912
Met Pro Leu Ser Asn Ala Lys Glu Thr Phe Asn Pro Leu Val Ala Ala
    290                 295                 300
```

```
ttt cca tca gta aat gtt agt tta gaa aag gtg att tta tcc aaa aat    960
Phe Pro Ser Val Asn Val Ser Leu Glu Lys Val Ile Leu Ser Lys Asn
305             310                 315                 320 gaa gac ctt tcc cat agc gtt gaa agc agt caa tct acc aat tgg tct   1008
Glu Asp Leu Ser His Ser Val Glu Ser Ser Gln Ser Thr Asn Trp Ser
            325                 330                 335 tat acc aat act gaa ggc gtt aac gtc aat gcc gga tgg tca ggc tta   1056
Tyr Thr Asn Thr Glu Gly Val Asn Val Asn Ala Gly Trp Ser Gly Leu
        340                 345                 350 gga cct agt ttt gga gtt tct gtt aac tat caa cat agt gaa act gta   1104
Gly Pro Ser Phe Gly Val Ser Val Asn Tyr Gln His Ser Glu Thr Val
    355                 360                 365 gca aat gaa tgg ggt tct gcg acg aat gat ggc aca cat ata aat gga   1152
Ala Asn Glu Trp Gly Ser Ala Thr Asn Asp Gly Thr His Ile Asn Gly
370                 375                 380 gcg gaa tct gct tat tta aac gca aat gtt cgc tat aat aac gtt ggg   1200
Ala Glu Ser Ala Tyr Leu Asn Ala Asn Val Arg Tyr Asn Asn Val Gly
385                 390                 395                 400 aca gga gca att tat gaa acg aaa cca aca acg agt ttt att ctt gat   1248
Thr Gly Ala Ile Tyr Glu Thr Lys Pro Thr Thr Ser Phe Ile Leu Asp
            405                 410                 415 gga aca aca att gga acg att aaa gca aaa gaa aat aca aca gct tta   1296
Gly Thr Thr Ile Gly Thr Ile Lys Ala Lys Glu Asn Thr Thr Ala Leu
        420                 425                 430 act att tta ccg gac caa agc tat cca gag aaa ggg aaa aac gga atc   1344
Thr Ile Leu Pro Asp Gln Ser Tyr Pro Glu Lys Gly Lys Asn Gly Ile
    435                 440                 445 gca att aac aca atg gat gat ttt aac tct cgc cca att cca tta aat   1392
Ala Ile Asn Thr Met Asp Asp Phe Asn Ser Arg Pro Ile Pro Leu Asn
450                 455                 460 aaa gag caa cta aat act tat tta tct aat aaa aaa cca atc cta ctt   1440
Lys Glu Gln Leu Asn Thr Tyr Leu Ser Asn Lys Lys Pro Ile Leu Leu
465                 470                 475                 480 gaa aca gat caa gta gaa gga aaa tac gcc ata aag gat acc aat ggg   1488
Glu Thr Asp Gln Val Glu Gly Lys Tyr Ala Ile Lys Asp Thr Asn Gly
            485                 490                 495 aat att aca ata gct gga gat tgg aat ggt ata aca gat gaa att tct   1536
Asn Ile Thr Ile Ala Gly Asp Trp Asn Gly Ile Thr Asp Glu Ile Ser
        500                 505                 510 gct aaa acg gcc tct att att gta gat aat gga aat caa atg tca gaa   1584
Ala Lys Thr Ala Ser Ile Ile Val Asp Asn Gly Asn Gln Met Ser Glu
    515                 520                 525 aag aga gtt gca gcg aag gat tat aca aat cca gag gat aaa act cct   1632
Lys Arg Val Ala Ala Lys Asp Tyr Thr Asn Pro Glu Asp Lys Thr Pro
530                 535                 540 aat tta tct gta aaa gaa gct cta aag tta gct tat cca gat gaa att   1680
Asn Leu Ser Val Lys Glu Ala Leu Lys Leu Ala Tyr Pro Asp Glu Ile
545                 550                 555                 560 gag gaa aaa gat ggt tta tta ttt tat aat gac caa cct att ttt gaa   1728
Glu Glu Lys Asp Gly Leu Leu Phe Tyr Asn Asp Gln Pro Ile Phe Glu
            565                 570                 575 gca tct gta caa agt tat gtt gac gaa tat aca gct aaa caa att aga   1776
Ala Ser Val Gln Ser Tyr Val Asp Glu Tyr Thr Ala Lys Gln Ile Arg
        580                 585                 590 aaa cag tta aat gat agt act ggt agc ttc aaa gat gtt aag aat tta   1824
Lys Gln Leu Asn Asp Ser Thr Gly Ser Phe Lys Asp Val Lys Asn Leu
    595                 600                 605 tat gat gtg aaa tta gaa ccc aaa atg aat ttc aca ata aaa act agc   1872
Tyr Asp Val Lys Leu Glu Pro Lys Met Asn Phe Thr Ile Lys Thr Ser
610                 615                 620
```

```
act tta tat gat gga gga gaa tct gac aac aca aaa ata gga aat tgg      1920
Thr Leu Tyr Asp Gly Gly Glu Ser Asp Asn Thr Lys Ile Gly Asn Trp
625             630                 635                 640 tac tat act tat gtt gtc aac gga gga aat acg ggt aaa aaa caa tac      1968
Tyr Tyr Thr Tyr Val Val Asn Gly Gly Asn Thr Gly Lys Lys Gln Tyr
                645                 650                 655 cgt tca gct aat aaa ggt gcc ttt act gag ctg tca aca gaa tca aag      2016
Arg Ser Ala Asn Lys Gly Ala Phe Thr Glu Leu Ser Thr Glu Ser Lys
            660                 665                 670 aat aaa ttg aaa aaa aat ata gat tac tac gta agc cta tat atg aag      2064
Asn Lys Leu Lys Lys Asn Ile Asp Tyr Tyr Val Ser Leu Tyr Met Lys
        675                 680                 685 gct gac tca aag gtt tca gtt gat ata gaa ata gac gga aaa cag gag      2112
Ala Asp Ser Lys Val Ser Val Asp Ile Glu Ile Asp Gly Lys Gln Glu
    690                 695                 700 tca att gta aca gat aat ata acc tta gat cac gta ggt tac caa aga      2160
Ser Ile Val Thr Asp Asn Ile Thr Leu Asp His Val Gly Tyr Gln Arg
705             710                 715                 720 ata aac atc cta gtc ccc aat ctg gaa gga aac gaa ata aat act att      2208
Ile Asn Ile Leu Val Pro Asn Leu Glu Gly Asn Glu Ile Asn Thr Ile
                725                 730                 735 tct att aaa ggt gac gga caa acc aat gtt tat tgg gat gat gtc tcc      2256
Ser Ile Lys Gly Asp Gly Gln Thr Asn Val Tyr Trp Asp Asp Val Ser
            740                 745                 750 ttt gtc gaa gtg gga gca gaa gaa att gaa tat aaa gat cca gtt ccc      2304
Phe Val Glu Val Gly Ala Glu Glu Ile Glu Tyr Lys Asp Pro Val Pro
        755                 760                 765 caa ttt gac att ata gaa gga gat ttt gat ttc ttt ggt gat cca ttg      2352
Gln Phe Asp Ile Ile Glu Gly Asp Phe Asp Phe Phe Gly Asp Pro Leu
    770                 775                 780 gcg gta aaa tat cat gat gca acg tat ttt ata gat agt cct ttg att      2400
Ala Val Lys Tyr His Asp Ala Thr Tyr Phe Ile Asp Ser Pro Leu Ile
785             790                 795                 800 aca caa act cct gga act ttc tcc ttt act tat aaa gtg att ggg gaa      2448
Thr Gln Thr Pro Gly Thr Phe Ser Phe Thr Tyr Lys Val Ile Gly Glu
                805                 810                 815 caa acg aag aca gta tta gat tcg gga tct ggt aaa aac gca aat cga      2496
Gln Thr Lys Thr Val Leu Asp Ser Gly Ser Gly Lys Asn Ala Asn Arg
            820                 825                 830 atc aac cta gat ttt aaa aat gta aaa tca gat cgt tca ttc tta tat      2544
Ile Asn Leu Asp Phe Lys Asn Val Lys Ser Asp Arg Ser Phe Leu Tyr
        835                 840                 845 aca tta tca tgt aaa gat gat tta tgg gga agc act cgc aca gca gtt      2592
Thr Leu Ser Cys Lys Asp Asp Leu Trp Gly Ser Thr Arg Thr Ala Val
    850                 855                 860 gtt aga att ttt gct gta gat taa                                      2616
Val Arg Ile Phe Ala Val Asp
865             870

<210> SEQ ID NO 2
<211> LENGTH: 871
<212> TYPE: PRT
<213> ORGANISM: Brevibacillus laterosporus

<400> SEQUENCE: 2

Met Lys Tyr Met Lys Lys Gly Leu Ser Ser Val Val Ile Gly Thr Leu
1               5                   10                  15

Phe Ala Ser Met Phe Leu Asn Gly Asn Val Asn Ala Val Tyr Ala Asn
                20                  25                  30

Ser Lys Thr Asn Gln Ile Ala Thr Thr Gln Ala Ser Lys Asp Asn
            35                  40                  45
```

```
Gln Ile Asp Arg Glu Gly Leu Leu Gly Tyr Tyr Phe Lys Gly Lys Asp
 50                  55                  60

Phe Asn Asp Leu Thr Leu Phe Ala Pro Thr Arg Asp Asn Thr Leu Ile
 65                  70                  75                  80

Tyr Asp Gln Gln Thr Ala Asn Thr Leu Val Asp Gln Lys His Gln Glu
                 85                  90                  95

Tyr His Ser Ile Arg Trp Ile Gly Leu Ile Gln Ser Ser Ala Thr Gly
                100                 105                 110

Asp Phe Thr Phe Lys Leu Ser Asp Asp Glu Asn Ala Ile Ile Glu Leu
            115                 120                 125

Asp Gly Lys Val Ile Ser Glu Lys Gly Asn Asn Lys Gln Ser Val His
        130                 135                 140

Leu Glu Lys Gly Gln Leu Val Gln Ile Lys Ile Glu Tyr Gln Ser Asp
145                 150                 155                 160

Asp Ala Leu His Ile Asp Asn Lys Ile Phe Lys Glu Leu Lys Leu Phe
                165                 170                 175

Lys Ile Asp Ser Gln Asn His Ser Gln Val Gln Asp Glu Leu
            180                 185                 190

Arg Asn Pro Glu Phe Asn Lys Lys Glu Thr Gln Val Phe Leu Lys Lys
        195                 200                 205

Ala Ser Lys Thr Asn Leu Phe Thr Gln Lys Thr Lys Arg Asp Ile Asp
210                 215                 220

Glu Asp Thr Asp Thr Asp Gly Asp Ser Ile Pro Asp Val Trp Glu Glu
225                 230                 235                 240

Asn Gly Tyr Thr Ile Gln Asn Lys Val Ala Val Lys Trp Asp Asp Ser
                245                 250                 255

Leu Ala Ser Lys Gly Tyr Gln Lys Phe Thr Ser Asn Pro Leu Glu Ala
            260                 265                 270

His Thr Val Gly Asp Pro Tyr Ser Asp Tyr Glu Lys Ala Ala Arg Asp
        275                 280                 285

Met Pro Leu Ser Asn Ala Lys Glu Thr Phe Asn Pro Leu Val Ala Ala
        290                 295                 300

Phe Pro Ser Val Asn Val Ser Leu Glu Lys Val Ile Leu Ser Lys Asn
305                 310                 315                 320

Glu Asp Leu Ser His Ser Val Glu Ser Ser Gln Ser Thr Asn Trp Ser
                325                 330                 335

Tyr Thr Asn Thr Glu Gly Val Asn Val Asn Ala Gly Trp Ser Gly Leu
            340                 345                 350

Gly Pro Ser Phe Gly Val Ser Val Asn Tyr Gln His Ser Glu Thr Val
        355                 360                 365

Ala Asn Glu Trp Gly Ser Ala Thr Asn Asp Gly Thr His Ile Asn Gly
        370                 375                 380

Ala Glu Ser Ala Tyr Leu Asn Ala Asn Val Arg Tyr Asn Asn Val Gly
385                 390                 395                 400

Thr Gly Ala Ile Tyr Glu Thr Lys Pro Thr Thr Ser Phe Ile Leu Asp
                405                 410                 415

Gly Thr Thr Ile Gly Thr Ile Lys Ala Lys Glu Asn Thr Thr Ala Leu
            420                 425                 430

Thr Ile Leu Pro Asp Gln Ser Tyr Pro Glu Lys Gly Lys Asn Gly Ile
        435                 440                 445

Ala Ile Asn Thr Met Asp Asp Phe Asn Ser Arg Pro Ile Pro Leu Asn
        450                 455                 460

Lys Glu Gln Leu Asn Thr Tyr Leu Ser Asn Lys Lys Pro Ile Leu Leu
465                 470                 475                 480
```

```
Glu Thr Asp Gln Val Glu Gly Lys Tyr Ala Ile Lys Asp Thr Asn Gly
            485                 490                 495

Asn Ile Thr Ile Ala Gly Asp Trp Asn Gly Ile Thr Asp Glu Ile Ser
        500                 505                 510

Ala Lys Thr Ala Ser Ile Ile Val Asp Asn Gly Asn Gln Met Ser Glu
    515                 520                 525

Lys Arg Val Ala Ala Lys Asp Tyr Thr Asn Pro Glu Asp Lys Thr Pro
530                 535                 540

Asn Leu Ser Val Lys Glu Ala Leu Lys Leu Ala Tyr Pro Asp Glu Ile
545                 550                 555                 560

Glu Glu Lys Asp Gly Leu Leu Phe Tyr Asn Asp Gln Pro Ile Phe Glu
                565                 570                 575

Ala Ser Val Gln Ser Tyr Val Asp Glu Tyr Thr Ala Lys Gln Ile Arg
            580                 585                 590

Lys Gln Leu Asn Asp Ser Thr Gly Ser Phe Lys Asp Val Lys Asn Leu
        595                 600                 605

Tyr Asp Val Lys Leu Glu Pro Lys Met Asn Phe Thr Ile Lys Thr Ser
    610                 615                 620

Thr Leu Tyr Asp Gly Gly Glu Ser Asp Asn Thr Lys Ile Gly Asn Trp
625                 630                 635                 640

Tyr Tyr Thr Tyr Val Val Asn Gly Gly Asn Thr Gly Lys Lys Gln Tyr
                645                 650                 655

Arg Ser Ala Asn Lys Gly Ala Phe Thr Glu Leu Ser Thr Glu Ser Lys
            660                 665                 670

Asn Lys Leu Lys Lys Asn Ile Asp Tyr Tyr Val Ser Leu Tyr Met Lys
        675                 680                 685

Ala Asp Ser Lys Val Ser Val Asp Ile Glu Ile Asp Gly Lys Gln Glu
    690                 695                 700

Ser Ile Val Thr Asp Asn Ile Thr Leu Asp His Val Gly Tyr Gln Arg
705                 710                 715                 720

Ile Asn Ile Leu Val Pro Asn Leu Glu Gly Asn Glu Ile Asn Thr Ile
                725                 730                 735

Ser Ile Lys Gly Asp Gly Gln Thr Asn Val Tyr Trp Asp Asp Val Ser
            740                 745                 750

Phe Val Glu Val Gly Ala Glu Glu Ile Glu Tyr Lys Asp Pro Val Pro
        755                 760                 765

Gln Phe Asp Ile Ile Glu Gly Asp Phe Asp Phe Gly Asp Pro Leu
    770                 775                 780

Ala Val Lys Tyr His Asp Ala Thr Tyr Phe Ile Asp Ser Pro Leu Ile
785                 790                 795                 800

Thr Gln Thr Pro Gly Thr Phe Ser Phe Thr Tyr Lys Val Ile Gly Glu
                805                 810                 815

Gln Thr Lys Thr Val Leu Asp Ser Gly Ser Gly Lys Asn Ala Asn Arg
            820                 825                 830

Ile Asn Leu Asp Phe Lys Asn Val Lys Ser Asp Arg Ser Phe Leu Tyr
        835                 840                 845

Thr Leu Ser Cys Lys Asp Asp Leu Trp Gly Ser Thr Arg Thr Ala Val
    850                 855                 860

Val Arg Ile Phe Ala Val Asp
865                 870

<210> SEQ ID NO 3
<211> LENGTH: 1374
<212> TYPE: DNA
<213> ORGANISM: Brevibacillus laterosporus
```

```
<220> FEATURE:
<221> NAME/KEY: CDS
<222> LOCATION: (1)..(1371)

<400> SEQUENCE: 3 atg att gtg att att ttc aca aac gta aaa gga ggg aat gag ttg aaa      48
Met Ile Val Ile Ile Phe Thr Asn Val Lys Gly Gly Asn Glu Leu Lys
1               5                   10                  15 aag aat ttt tat aag aat ctt att tgt atg tct gct tta ttg tta gcc      96
Lys Asn Phe Tyr Lys Asn Leu Ile Cys Met Ser Ala Leu Leu Leu Ala
            20                  25                  30 atg cct ata tca agc aac gtt acg tac gct tac ggt agt gag aag gtt     144
Met Pro Ile Ser Ser Asn Val Thr Tyr Ala Tyr Gly Ser Glu Lys Val
        35                  40                  45 gat tat tta gta aaa acg act aac aat aca gag gat ttt aaa gag gat     192
Asp Tyr Leu Val Lys Thr Thr Asn Asn Thr Glu Asp Phe Lys Glu Asp
    50                  55                  60 aag gaa aaa gcc aaa gaa tgg ggg aaa gaa aaa gag aaa gag tgg aaa     240
Lys Glu Lys Ala Lys Glu Trp Gly Lys Glu Lys Glu Lys Glu Trp Lys
65                  70                  75                  80 cta act gtt act gaa aaa aca agg atg aat aat ttt tta gat aat aaa     288
Leu Thr Val Thr Glu Lys Thr Arg Met Asn Asn Phe Leu Asp Asn Lys
                85                  90                  95 aat gat ata aaa aaa aat tat aaa gaa att act ttt tct atg gca ggt     336
Asn Asp Ile Lys Lys Asn Tyr Lys Glu Ile Thr Phe Ser Met Ala Gly
            100                 105                 110 tca ttt gaa gat gaa ata aaa gat tta aaa gag att gat aaa atg ttt     384
Ser Phe Glu Asp Glu Ile Lys Asp Leu Lys Glu Ile Asp Lys Met Phe
        115                 120                 125 gat aaa gcc aat cta tca agt tct att gtc acc tat aaa aat gtg gag     432
Asp Lys Ala Asn Leu Ser Ser Ser Ile Val Thr Tyr Lys Asn Val Glu
    130                 135                 140 ccc tca acg att gga ttt aac aaa cct tta aca gaa ggt aat act att     480
Pro Ser Thr Ile Gly Phe Asn Lys Pro Leu Thr Glu Gly Asn Thr Ile
145                 150                 155                 160 aat act gat gta caa gcc cag ttt aaa gaa caa ttt tta gga aaa gat     528
Asn Thr Asp Val Gln Ala Gln Phe Lys Glu Gln Phe Leu Gly Lys Asp
                165                 170                 175 att aag ttt gat agt tat ctt gac act cac tta act gca caa aat gtt     576
Ile Lys Phe Asp Ser Tyr Leu Asp Thr His Leu Thr Ala Gln Asn Val
            180                 185                 190 tct agt aaa gaa aga att att tta caa gtt aca gtg cca agt ggt aaa     624
Ser Ser Lys Glu Arg Ile Ile Leu Gln Val Thr Val Pro Ser Gly Lys
        195                 200                 205 gga tct act att cca aca aaa gca ggt gta att tta aat aat aat gag     672
Gly Ser Thr Ile Pro Thr Lys Ala Gly Val Ile Leu Asn Asn Asn Glu
    210                 215                 220 tat aaa atg cta att gat aat ggc tat gta ctc cat gtg gat aat ata     720
Tyr Lys Met Leu Ile Asp Asn Gly Tyr Val Leu His Val Asp Asn Ile
225                 230                 235                 240 tcg aaa gta gta aaa aaa ggt tat gaa tgt tta caa att caa gga acg     768
Ser Lys Val Val Lys Lys Gly Tyr Glu Cys Leu Gln Ile Gln Gly Thr
                245                 250                 255 cta aaa aag agt ctc gat ttt aaa aat gat att aat gct gag gct cat     816
Leu Lys Lys Ser Leu Asp Phe Lys Asn Asp Ile Asn Ala Glu Ala His
            260                 265                 270 cgt tgg ggt atg aaa aat tat gaa gga tgg gct aaa aat tta aca gat     864
Arg Trp Gly Met Lys Asn Tyr Glu Gly Trp Ala Lys Asn Leu Thr Asp
        275                 280                 285
```

```
cct caa agg gaa gct tta gat ggg tat gct aga caa gat tat aaa caa       912
Pro Gln Arg Glu Ala Leu Asp Gly Tyr Ala Arg Gln Asp Tyr Lys Gln
    290                 295                 300 ata aat gat tat tta cga aat caa ggt gga agt gga aat gaa aaa cta       960
Ile Asn Asp Tyr Leu Arg Asn Gln Gly Gly Ser Gly Asn Glu Lys Leu
305                 310                 315                 320 gat aca caa ata aaa aat att tct gaa gca tta gaa aag cag cca ata      1008
Asp Thr Gln Ile Lys Asn Ile Ser Glu Ala Leu Glu Lys Gln Pro Ile
                325                 330                 335 cca gaa aat att act gtg tat aga tgg tgt gga atg gcg gaa ttt ggt      1056
Pro Glu Asn Ile Thr Val Tyr Arg Trp Cys Gly Met Ala Glu Phe Gly
            340                 345                 350 tat caa att agt gat cct tta cct tct tta aaa gaa atg gaa gaa aaa      1104
Tyr Gln Ile Ser Asp Pro Leu Pro Ser Leu Lys Glu Met Glu Glu Lys
        355                 360                 365 ttt tta aat aca atg aaa gaa gat aag gga tat atg agt act agt ttg      1152
Phe Leu Asn Thr Met Lys Glu Asp Lys Gly Tyr Met Ser Thr Ser Leu
    370                 375                 380 tca agt gaa cgt ctt tct gca ttt ggt tcg aga aaa ttc att tta aga      1200
Ser Ser Glu Arg Leu Ser Ala Phe Gly Ser Arg Lys Phe Ile Leu Arg
385                 390                 395                 400 tta caa gtt cct aaa gga agc aca ggg gca tat tta agc gct att ggg      1248
Leu Gln Val Pro Lys Gly Ser Thr Gly Ala Tyr Leu Ser Ala Ile Gly
                405                 410                 415 gga ttt gca agt gaa aaa gaa atc ctt att gat aaa gat agt aac tat      1296
Gly Phe Ala Ser Glu Lys Glu Ile Leu Ile Asp Lys Asp Ser Asn Tyr
            420                 425                 430 cat att gat aaa ata aca gag gta gtc att aaa ggt gtt aag cga tat      1344
His Ile Asp Lys Ile Thr Glu Val Val Ile Lys Gly Val Lys Arg Tyr
        435                 440                 445 gta gtt gat gca acg tta tta aca aaa taa                              1374
Val Val Asp Ala Thr Leu Leu Thr Lys
    450                 455
```

<210> SEQ ID NO 4
<211> LENGTH: 457
<212> TYPE: PRT
<213> ORGANISM: Brevibacillus laterosporus

<400> SEQUENCE: 4

```
Met Ile Val Ile Ile Phe Thr Asn Val Lys Gly Gly Asn Glu Leu Lys
1               5                   10                  15

Lys Asn Phe Tyr Lys Asn Leu Ile Cys Met Ser Ala Leu Leu Leu Ala
            20                  25                  30

Met Pro Ile Ser Ser Asn Val Thr Tyr Ala Tyr Gly Ser Glu Lys Val
        35                  40                  45

Asp Tyr Leu Val Lys Thr Thr Asn Asn Thr Glu Asp Phe Lys Glu Asp
    50                  55                  60

Lys Glu Lys Ala Lys Glu Trp Gly Lys Glu Lys Glu Lys Glu Trp Lys
65                  70                  75                  80

Leu Thr Val Thr Glu Lys Thr Arg Met Asn Asn Phe Leu Asp Asn Lys
                85                  90                  95

Asn Asp Ile Lys Lys Asn Tyr Lys Glu Ile Thr Phe Ser Met Ala Gly
            100                 105                 110

Ser Phe Glu Asp Glu Ile Lys Asp Leu Lys Glu Ile Asp Lys Met Phe
        115                 120                 125

Asp Lys Ala Asn Leu Ser Ser Ser Ile Val Thr Tyr Lys Asn Val Glu
    130                 135                 140
```

-continued

| | | | | | | | | | | | | | | |
|---|---|---|---|---|---|---|---|---|---|---|---|---|---|---|
| Pro | Ser | Thr | Ile | Gly | Phe | Asn | Lys | Pro | Leu | Thr | Glu | Gly | Asn | Thr | Ile |
| 145 | | | | 150 | | | | | 155 | | | | | 160 | |
| Asn | Thr | Asp | Val | Gln | Ala | Gln | Phe | Lys | Glu | Gln | Phe | Leu | Gly | Lys | Asp |
| | | | | 165 | | | | | 170 | | | | | 175 | |
| Ile | Lys | Phe | Asp | Ser | Tyr | Leu | Asp | Thr | His | Leu | Thr | Ala | Gln | Asn | Val |
| | | | 180 | | | | | 185 | | | | | 190 | | |
| Ser | Ser | Lys | Glu | Arg | Ile | Ile | Leu | Gln | Val | Thr | Val | Pro | Ser | Gly | Lys |
| | | 195 | | | | | 200 | | | | | 205 | | | |
| Gly | Ser | Thr | Ile | Pro | Thr | Lys | Ala | Gly | Val | Ile | Leu | Asn | Asn | Asn | Glu |
| 210 | | | | | 215 | | | | | 220 | | | | | |
| Tyr | Lys | Met | Leu | Ile | Asp | Asn | Gly | Tyr | Val | Leu | His | Val | Asp | Asn | Ile |
| 225 | | | | | 230 | | | | | 235 | | | | | 240 |
| Ser | Lys | Val | Val | Lys | Gly | Tyr | Glu | Cys | Leu | Gln | Ile | Gln | Gly | Thr | |
| | | | | 245 | | | | | 250 | | | | | 255 | |
| Leu | Lys | Lys | Ser | Leu | Asp | Phe | Lys | Asn | Asp | Ile | Asn | Ala | Glu | Ala | His |
| | | | 260 | | | | | 265 | | | | | 270 | | |
| Arg | Trp | Gly | Met | Lys | Asn | Tyr | Glu | Gly | Trp | Ala | Lys | Asn | Leu | Thr | Asp |
| | | 275 | | | | | 280 | | | | | 285 | | | |
| Pro | Gln | Arg | Glu | Ala | Leu | Asp | Gly | Tyr | Ala | Arg | Gln | Asp | Tyr | Lys | Gln |
| 290 | | | | | 295 | | | | | 300 | | | | | |
| Ile | Asn | Asp | Tyr | Leu | Arg | Asn | Gln | Gly | Gly | Ser | Gly | Asn | Glu | Lys | Leu |
| 305 | | | | | 310 | | | | | 315 | | | | | 320 |
| Asp | Thr | Gln | Ile | Lys | Asn | Ile | Ser | Glu | Ala | Leu | Glu | Lys | Gln | Pro | Ile |
| | | | | 325 | | | | | 330 | | | | | 335 | |
| Pro | Glu | Asn | Ile | Thr | Val | Tyr | Arg | Trp | Cys | Gly | Met | Ala | Glu | Phe | Gly |
| | | | 340 | | | | | 345 | | | | | 350 | | |
| Tyr | Gln | Ile | Ser | Asp | Pro | Leu | Pro | Ser | Leu | Lys | Glu | Met | Glu | Glu | Lys |
| | | 355 | | | | | 360 | | | | | 365 | | | |
| Phe | Leu | Asn | Thr | Met | Lys | Glu | Asp | Lys | Gly | Tyr | Met | Ser | Thr | Ser | Leu |
| 370 | | | | | 375 | | | | | 380 | | | | | |
| Ser | Ser | Glu | Arg | Leu | Ser | Ala | Phe | Gly | Ser | Arg | Lys | Phe | Ile | Leu | Arg |
| 385 | | | | | 390 | | | | | 395 | | | | | 400 |
| Leu | Gln | Val | Pro | Lys | Gly | Ser | Thr | Gly | Ala | Tyr | Leu | Ser | Ala | Ile | Gly |
| | | | | 405 | | | | | 410 | | | | | 415 | |
| Gly | Phe | Ala | Ser | Glu | Lys | Glu | Ile | Leu | Ile | Asp | Lys | Asp | Ser | Asn | Tyr |
| | | | 420 | | | | | 425 | | | | | 430 | | |
| His | Ile | Asp | Lys | Ile | Thr | Glu | Val | Val | Ile | Lys | Gly | Val | Lys | Arg | Tyr |
| | | 435 | | | | | 440 | | | | | 445 | | | |
| Val | Val | Asp | Ala | Thr | Leu | Leu | Thr | Lys | | | | | | | |
| 450 | | | | | 455 | | | | | | | | | | |

<210> SEQ ID NO 5
<211> LENGTH: 2658
<212> TYPE: DNA
<213> ORGANISM: Zea mays
<220> FEATURE:
<221> NAME/KEY: misc_feature
<222> LOCATION: (21)..()
<223> OTHER INFORMATION: Nucleotide at position 21 is "n" wherein
      "n" = any nucleotide

<400> SEQUENCE: 5
cctaaggccg atttcgtcct nagcagggcc caaaggaagg aagtacttca gtggatcaag      60
atgttgatgt tccctgatgg gtatgcagct aacctgagta ggtggggtga acttatctac     120
tctgtgagtc ttagggatga agagtcatga cttccacata tggattgaac agattcttct     180
ctgtgcatgg acaatctggg gcggcatcca acaaccctca tggatcgccc ggccaatcgc     240

```
cgcaccagtc catccgccca cctcgatgag acttatgttc ttagtgttga gacttcagaa     300
cttattgata atgctgtatt ggatacttat gtttgtgttc gatacttatg tgagaacttg     360
agacttatga gacttatgtt cttgatactt atgtttgtgt tgagaacttg gatatttatg     420
tttgtgttgg atacttatgt ctgtgatgat atatgtgatg tatatatgtg atgtatatgt     480
gacatatgtg atgtatatgt ggtatctttt gtttgtttgg atggaataga gaaagcaaat     540
aaaaatgtgt atactggtca ctttgtcgag tgtaacactc ggcaaaaagg tgctttgccg     600
agtgttaggg ccatagcact cggtagagaa ccaatactta ggcaccggta agctttttt      660 ggcgagtgtt gtggccctgg cactcagctt gccgagtgc ctcacagagc actcgacaaa      720
gaacctgaca aatggacccg ctggtaaatc ctttaccgag tgcaggtcag tagacactcg     780
gcaaaggtaa cttctttgcc gagtgccgct tagaacattt gacaaagggt catctccgtt     840
acccggtgtc gtgacggccg cttttctttg ccgagtgcct gatagaaagt actcggcaaa     900
gaagtcgttg ccaatgtatt gttcgctgag gtctctttgt caagtattac actcggcaaa     960
gactgtgccg agtgtttttc agactttgcc gagtggttta agcactcagc aaagcgctcg    1020
atttcggtag tgacggttgt ttggcaatag taaaatccag ccctctcccg tggggaaaaa    1080
actggtagga tctggctcgt ggctaagatt ctctttcttc cctttgtaaa aaagagaag     1140 aaaaaaaaaa cgactgtcac ggtgccttgt ctggtaatga tcgcgcggtc ggctctgtcc    1200
taacccgtaa gatggacggg agctgatgat agcgtgacct ccaaataaac aacaagggcg    1260
tgttccccgc ggtcgaatat tttaagggcc actgattagg tgcggttgaa tacatcaact    1320
tcacgaacat catctgatct gatctgattt ggtctgatat gatctgggta gtcatttctg    1380
caatgagcat ctatcaggtg aaccaattaa tattgatgac attatgagtt cgaagatata    1440
ctctaaagtg ttatctaaat acagaagaca ttcgttcgtt cttgcctat aactctaaaa      1500 ggcttgtaac accctcattc atcctctata tacgaagact ctctcctatc attttatcg      1560 atttatttt tttatattta gacaatggaa ttaaatagaa ctaaaatata taagatga       1620 tatctgagga cccagatgg taatggggac tcgatcctcg attctccacg gagaattcct      1680
ctaggatata ggtaatttgt ccccacgagg attgaaacgg ggtaatttgg tccccatgtg    1740
cccgtcccgc gaacttctct tgatctaaat tagtctattt ccatgttaaa actatactaa    1800
aaatttaata cacagtctat tataaaatag caaactaaat tctaaagttg atgcatcttg    1860
taattttaaa tctggtttgt tcaagttata ttcatttgat ataataaatt tgaatttgac    1920
tcttaatatc gtatttttc ctaacgggga cggattctcc acgggataa attccatgat      1980 acagatggga tgaaagaaaa atctcccgta tgaacttttg caggaatggg gatgggccag    2040 agaaatttc tccctgcggg gacgggggag ccatatcctc ggtggagaat tcccattat      2100 catccttatt tgtggtacat atatatgcat aatcttttt ttttgactga catgtgggaa     2160
agtatcccat ctcaatagta gaaaatcttg ggaacggtag gatcgaacac aaagatcagc    2220
tagcttgtaa tcaccgagcc atatagctag agggtaatag atcatgaatc aaatgttttt    2280
ttcataaatt attaaggctc taaattattt ttaatttaaa aataaataaa aatatagttc    2340
gattcttaca ttttatagtg taaaacttta agtctatta ttaccctac ttattgagtt      2400 atggttcagt tcttgtcgac ggagagtaat gagatataga ataaggtacc ctatagaata    2460
aagaatcttt ctctgaaaag tctgacgtac gtaaataaga tataataaaa aaaatacaaa    2520
gagaagcgct ggactggaga tgctcctata tgcggcaatg cctgtgctta taaatagcca    2580
```

-continued

| | |
|---|---|
| cctcggtcgg caaggacatg aacggcggac gcagtgtgca tgcatacaag agcaacaaga | 2640 |
| tactggcgca gaggagca | 2658 |

<210> SEQ ID NO 6
<211> LENGTH: 4325
<212> TYPE: DNA
<213> ORGANISM: Zea Mays
<220> FEATURE:
<221> NAME/KEY: misc_feature
<222> LOCATION: (372)..(1688)
<223> OTHER INFORMATION: Nucleotides at positions 372, 525, 586, 714, 737, 747, 754, 785, and 1688 are "n" wherein "n" = any nucleotide

<400> SEQUENCE: 6

| | |
|---|---|
| gcggccgcgg aattaaccct cactaaaggg aacgaattcg gatccctgtg gagaaatttt | 60 |
| tacgtcgcgg ggatggtatg gggagttatt cccctgtagg aaatgggtga cgcctaagag | 120 |
| ggagggtgaa gtaggacttc taaaactttc actaaactag gccacaaata attccctaga | 180 |
| gcaaaaccta tgcaaatagt caaactagaa tgtgcaaacc aagttttgtc taagtgttgc | 240 |
| tatctctacc gcaatggcta agtttcaatc tacactatat aagtatgaat acaagaatga | 300 |
| aacttaaata cttaatataa atgcggaaac ttaaagagca aggtagagat gcaaattctc | 360 |
| gtggatgacg cntgcatttt tatcgaggta tccggaacca cgcaaggtcc cgactaatcc | 420 |
| tcattggtgc ccctacgcaa agggaagccc acgcgagggc caagcacctc ggtcgagtaa | 480 |
| ctcttataga gagccgtggg ccttctccac gcgcaagtgg tgctntgctt tcagctcctc | 540 |
| tcagaccctc cccgctgtct ccactatcga gcttccggct gaaaangcca tgggcctcgt | 600 |
| tccctccggt acacggtggc ggccgtgaca caaatgcggt tatcacgggt ctcgcaagac | 660 |
| tctcacccccc actggggaca aatttcaatg gctcgcacaa gagccgaggg gttnatggtt | 720 |
| tatctaatct cactcanctt aactagnatt catntaaagc aagcgctaga gcggtctaac | 780 |
| taacntaagc acttcacaaa gcacctacgc ttaatcaccg agtgattcta tttagcactt | 840 |
| gggtgcaaga gcacttgaga atgtctacta tatgccttgc tatgtctctt gggctcccaa | 900 |
| acttggaaat ggccggttgg tggtgtattt atagccccca acacaaaact agccgttgga | 960 |
| ggaagctgct gcttttgtg gtgcaccgga cagtccggtg gggtcaccag acagtccgac | 1020 |
| gccctgtcc ggtgccctg tccgatgcgc ctagttgttg ggtctgtcag cgtaggtgac | 1080 |
| cgttggcgcg caggcttttt gcaccggaca gtccggtggt cttccctcga cagtgccacc | 1140 |
| tggagctagc cgttagggct actgttcctg gtgcaccgga cagtagtccg gtgctcttgt | 1200 |
| ttggacagtc cgacttgtgg caacacttct tcttttcttg gactttactt gatcttcatg | 1260 |
| atgtcttctt ttgaggtgtt gctttcctaa gtgccttggt ccaagtaact tatcatcctg | 1320 |
| tgaactacaa acacaaatag tagcaaacac attagtccac aggttatgtt gatcatcaaa | 1380 |
| taccaaaatc tattaagcca aatggcccag ggtccatttt ccttacatcc ccgacgaaga | 1440 |
| attctccgtt gccatcccta tctgtgtacg cactactgga atccgggtct ttgctgagta | 1500 |
| ccgcactcgg caaagtccta ctctcggtaa cgatgccttt tgccgagagc aggactctcg | 1560 |
| gcacaggaat acactcggcg aagggcgggt ctcggcaaag gccgttagcc accgtccaaa | 1620 |
| gctgacggtc gttacctatg ccgagtggtg gaaagatatt gtgaaggcct aaggccgatt | 1680 |
| tcgtcctnag cagggcccaa aggaaggaag tacttcagtg gatcaagatg ttgatgttcc | 1740 |
| ctgatgggta tgcagctaac ctgagtaggt ggggtgaact tatctactct gtgagtctta | 1800 |
| gggatgaaga gtcatgactt ccacatatgg attgaacaga ttcttctctg tgcatggaca | 1860 |
| atctggggcg gcatccaaca accctcatgg atcgcccggc caatcgccgc accagtccat | 1920 |

```
ccgcccacct cgatgagact tatgttctta gtgttgagac ttcagaactt attgataatg    1980
ctgtattgga tacttatgtt tgtgttcgat acttatgtga gaacttgaga cttatgagac    2040
ttatgttctt gatacttatg tttgtgttga gaacttggat atttatgttt gtgttggata    2100
cttatgtctg tgatgatata tgtgatgtat atatgtgatg tatatgtgac atatgtgatg    2160
tatatgtggt atcttttgtt tgtttggatg gaatagagaa agcaaataaa aatgtgtata    2220
ctggtcactt tgtcgagtgt aacactcggc aaaaaggtgc tttgccgagt gttagggcca    2280
tagcactcgg tagagaacca atacttaggc accggtaaag ctttttttggc gagtgttgtg    2340 gccctggcac tcagctttgc cgagtgcctc acagagcact cgacaaagaa cctgacaaat    2400
ggacccgctg gtaaatcctt taccgagtgc aggtcagtag acactcggca aaggtaactt    2460
ctttgccgag tgccgcttag aacatttgac aaagggtcat ctccgttacc cggtgtcgtg    2520
acggccgctt ttctttgccg agtgcctgat agaaagtact cggcaaagaa gtcgttgcca    2580
atgtattgtt cgctgaggtc tctttgtcaa gtattacact cggcaaagac tgtgccgagt    2640 gttttttcaga ctttgccgag tggtttaagc actcagcaaa gcgctcgatt tcggtagtga    2700
cggttgtttg gcaatagtaa aatccagccc tctcccgtgg ggaaaaaact ggtaggatct    2760
ggctcgtggc taagattctc tttcttccct ttgtaaaaaa agagaagaaa aaaaaaacga    2820
ctgtcacggt gccttgtctg gtaatgatcg cgcggtcggc tctgtcctaa cccgtaagat    2880
ggacgggagc tgatgatagc gtgacctcca aataaacaac aagggcgtgt tccccgcgt    2940 cgaatatttt aagggccact gattaggtgc ggttgaatac atcaacttca cgaacatcat    3000
ctgatctgat ctgatttggt ctgatatgat ctgggtagtc atttctgcaa tgagcatcta    3060
tcaggtgaac caattaatat tgatgacatt atgagttcga agatatactc taaagtgtta    3120
tctaaataca gaagacattc gttcgttctt tgcctataac tctaaaaggc ttgtaacacc    3180
ctcattcatc ctctatatac gaagactctc tcctatcatt tttatcgatt tattttttt    3240 atatttagac aatggaatta aatagaacta aaatatatat aagatgatat ctgaggaccc    3300
gagatggtaa tggggactcg atcctcgatt ctccacggag aattcctcta ggatataggt    3360
aatttgtccc cacgaggatt gaaacggggt aatttggtcc ccatgtgccc gtcccgcgaa    3420
cttctcttga tctaaattag tctatttcca tgttaaaact atactaaaaa tttaatacac    3480
agtctattat aaaatagcaa actaaattct aaagttgatg catcttgtaa ttttaaatct    3540
ggtttgttca agttatattc atttgatata ataaatttga atttgactct taatatcgta    3600
ttttttccta acggggacgg attctccacg gggataaatt ccatgataca gatgggatga    3660
aagaaaaatc tcccgtatga acttttgcag gaatggggat gggccagaga aattttctcc    3720
ctgcggggac gggggagcca tatcctcggt ggagaatttc ccattatcat ccttatttgt    3780
ggtacatata tatgcataat ctttttttttt tgactgacat gtgggaaagt atcccatctc    3840
aatagtagaa aatcttggga acggtaggat cgaacacaaa gatcagctag cttgtaatca    3900
ccgagccata tagctagagg gtaatagatc atgaatcaaa tgtttttttc ataaattatt    3960
aaggctctaa attattttta atttaaaaat aaataaaaat atagttcgat tcttacattt    4020
tatagtgtaa aactttaaag tctattatta cccctactta ttgagttatg gttcagttct    4080
tgtcgacgga gagtaatgag atatagaata aggtacccta tagaataaag aatctttctc    4140
tgaaaagtct gacgtacgta aataagatat aataaaaaaa atacaaagag aagcgctgga    4200
ctggagatgc tcctatatgc ggcaatgcct gtgcttataa atagccacct cggtcggcaa    4260
```

-continued

```
ggacatgaac ggcggacgca gtgtgcatgc atacaagagc aacaagatac tggcgcagag    4320
gagca                                                                4325

<210> SEQ ID NO 7
<211> LENGTH: 1239
<212> TYPE: DNA
<213> ORGANISM: Artificial Sequence
<220> FEATURE:
<223> OTHER INFORMATION: modified DNA encoding ISP2A protein
<220> FEATURE:
<221> NAME/KEY: CDS
<222> LOCATION: (3)..(1229)

<400> SEQUENCE: 7 cc atg gca cta gtg aag acc acc aac aac acc gag gac ttc aag gag        47
   Met Ala Leu Val Lys Thr Thr Asn Asn Thr Glu Asp Phe Lys Glu
   1               5                   10                  15 gac aag gag aag gcc aag gag tgg ggc aag gag aag gag aag gag tgg       95
Asp Lys Glu Lys Ala Lys Glu Trp Gly Lys Glu Lys Glu Lys Glu Trp
                20                  25                  30 aag ctg acc gtg acc gag aag acg cgt atg aat aat ttc ctg gac aac      143
Lys Leu Thr Val Thr Glu Lys Thr Arg Met Asn Asn Phe Leu Asp Asn
            35                  40                  45 aag aac gac atc aag aag aac tac aag gag atc acc ttc agc atg gct      191
Lys Asn Asp Ile Lys Lys Asn Tyr Lys Glu Ile Thr Phe Ser Met Ala
        50                  55                  60 ggc tcc ttc gag gac gag atc aag gac ctg aag gag atc gac aag atg      239
Gly Ser Phe Glu Asp Glu Ile Lys Asp Leu Lys Glu Ile Asp Lys Met
    65                  70                  75 ttc gac aag gcc aac ctg tcc tcc tcc atc gtg acc tac aag aac gtg      287
Phe Asp Lys Ala Asn Leu Ser Ser Ser Ile Val Thr Tyr Lys Asn Val
80                  85                  90                  95 gag cca tcc acc atc gga ttt aac aag cca ctg acc gag ggc aac acc      335
Glu Pro Ser Thr Ile Gly Phe Asn Lys Pro Leu Thr Glu Gly Asn Thr
                100                 105                 110 atc aac acc gac gtg cag gcc cag ttc aag gag cag ttc ctg ggc aag      383
Ile Asn Thr Asp Val Gln Ala Gln Phe Lys Glu Gln Phe Leu Gly Lys
            115                 120                 125 gac atc aag ttc gac tcc tac ctg gac acc cac ctg act gct cag aac      431
Asp Ile Lys Phe Asp Ser Tyr Leu Asp Thr His Leu Thr Ala Gln Asn
        130                 135                 140 gtg tcc tcc aag gag agg atc atc ctc caa gtg acc gtg cca tcc ggc      479
Val Ser Ser Lys Glu Arg Ile Ile Leu Gln Val Thr Val Pro Ser Gly
    145                 150                 155 aag ggc tcc acc atc ccg acc aag gct ggt gtg atc ctg aac aac aac      527
Lys Gly Ser Thr Ile Pro Thr Lys Ala Gly Val Ile Leu Asn Asn Asn
160                 165                 170                 175 gag tac aag atg ctg atc gac aac ggc tac gtg ctg cac gtg gac aac      575
Glu Tyr Lys Met Leu Ile Asp Asn Gly Tyr Val Leu His Val Asp Asn
                180                 185                 190 atc tcc aag gtg gtg aag aag ggt tac gag tgc ctg cag atc cag ggt      623
Ile Ser Lys Val Val Lys Lys Gly Tyr Glu Cys Leu Gln Ile Gln Gly
            195                 200                 205 acc ctg aag aag tcc ctg gac ttc aag aac gac atc aac gcc gag gct      671
Thr Leu Lys Lys Ser Leu Asp Phe Lys Asn Asp Ile Asn Ala Glu Ala
        210                 215                 220 cac agg tgg ggc atg aag aac tac gag ggt tgg gct aag aac ctg acc      719
His Arg Trp Gly Met Lys Asn Tyr Glu Gly Trp Ala Lys Asn Leu Thr
    225                 230                 235 gac cca cag agg gag gcc ctg gac ggc tac gct agg cag gac tac aag      767
Asp Pro Gln Arg Glu Ala Leu Asp Gly Tyr Ala Arg Gln Asp Tyr Lys
240                 245                 250                 255
```

-continued

```
cag atc aac gac tac ctg cgg aac cag ggt ggc tcc ggc aac gag aag      815
Gln Ile Asn Asp Tyr Leu Arg Asn Gln Gly Gly Ser Gly Asn Glu Lys
            260                 265                 270 ctg gac acc cag atc aag aac atc tcc gag gct ctg gag aag cag ccg      863
Leu Asp Thr Gln Ile Lys Asn Ile Ser Glu Ala Leu Glu Lys Gln Pro
        275                 280                 285 atc cca gag aac atc acc gtg tac agg tgg tgc ggt atg gcc gag ttc      911
Ile Pro Glu Asn Ile Thr Val Tyr Arg Trp Cys Gly Met Ala Glu Phe
    290                 295                 300 ggt tac cag att tcc gac cca ctg cca tcc ctg aag gag atg gag gag      959
Gly Tyr Gln Ile Ser Asp Pro Leu Pro Ser Leu Lys Glu Met Glu Glu
305                 310                 315 aag ttc ctg aac acc atg aag gag gac aag ggt tac atg tcc acc tcc     1007
Lys Phe Leu Asn Thr Met Lys Glu Asp Lys Gly Tyr Met Ser Thr Ser
320                 325                 330                 335 ctg tcc tcc gag agg ctg tcc gct ttc ggc tcc agg aag ttc atc ctg     1055
Leu Ser Ser Glu Arg Leu Ser Ala Phe Gly Ser Arg Lys Phe Ile Leu
                340                 345                 350 agg ctg cag gtg cca aag ggt tcc act ggt gcc tac ctg tcc gct atc     1103
Arg Leu Gln Val Pro Lys Gly Ser Thr Gly Ala Tyr Leu Ser Ala Ile
            355                 360                 365 ggt ggc ttc gct tcc gag aag gag atc ctg atc gac aag gac tcc aac     1151
Gly Gly Phe Ala Ser Glu Lys Glu Ile Leu Ile Asp Lys Asp Ser Asn
        370                 375                 380 tac cac atc gac aag atc acc gag gtg gtg atc aag ggt gtg aag agg     1199
Tyr His Ile Asp Lys Ile Thr Glu Val Val Ile Lys Gly Val Lys Arg
    385                 390                 395 tac gta gtg gac gct acc ctg ctg acc aag tgaggctagc                   1239
Tyr Val Val Asp Ala Thr Leu Leu Thr Lys
400                 405

<210> SEQ ID NO 8
<211> LENGTH: 409
<212> TYPE: PRT
<213> ORGANISM: Artificial Sequence
<220> FEATURE:
<223> OTHER INFORMATION: ISP2A protein

<400> SEQUENCE: 8

Met Ala Leu Val Lys Thr Thr Asn Asn Thr Glu Asp Phe Lys Glu Asp
1               5                   10                  15

Lys Glu Lys Ala Lys Glu Trp Gly Lys Glu Lys Glu Lys Glu Trp Lys
            20                  25                  30

Leu Thr Val Thr Glu Lys Thr Arg Met Asn Asn Phe Leu Asp Asn Lys
        35                  40                  45

Asn Asp Ile Lys Lys Asn Tyr Lys Glu Ile Thr Phe Ser Met Ala Gly
    50                  55                  60

Ser Phe Glu Asp Glu Ile Lys Asp Leu Lys Glu Ile Asp Lys Met Phe
65                  70                  75                  80

Asp Lys Ala Asn Leu Ser Ser Ile Val Thr Tyr Lys Asn Val Glu
                85                  90                  95

Pro Ser Thr Ile Gly Phe Asn Lys Pro Leu Thr Glu Gly Asn Thr Ile
            100                 105                 110

Asn Thr Asp Val Gln Ala Gln Phe Lys Glu Gln Phe Leu Gly Lys Asp
        115                 120                 125

Ile Lys Phe Asp Ser Tyr Leu Asp Thr His Leu Thr Ala Gln Asn Val
    130                 135                 140

Ser Ser Lys Glu Arg Ile Ile Leu Gln Val Thr Val Pro Ser Gly Lys
145                 150                 155                 160
```

```
Gly Ser Thr Ile Pro Thr Lys Ala Gly Val Ile Leu Asn Asn Asn Glu
                165                 170                 175

Tyr Lys Met Leu Ile Asp Asn Gly Tyr Val Leu His Val Asp Asn Ile
            180                 185                 190

Ser Lys Val Val Lys Lys Gly Tyr Glu Cys Leu Gln Ile Gln Gly Thr
        195                 200                 205

Leu Lys Lys Ser Leu Asp Phe Lys Asn Asp Ile Asn Ala Glu Ala His
    210                 215                 220

Arg Trp Gly Met Lys Asn Tyr Glu Gly Trp Ala Lys Asn Leu Thr Asp
225                 230                 235                 240

Pro Gln Arg Glu Ala Leu Asp Gly Tyr Ala Arg Gln Asp Tyr Lys Gln
                245                 250                 255

Ile Asn Asp Tyr Leu Arg Asn Gln Gly Gly Ser Gly Asn Glu Lys Leu
            260                 265                 270

Asp Thr Gln Ile Lys Asn Ile Ser Glu Ala Leu Glu Lys Gln Pro Ile
        275                 280                 285

Pro Glu Asn Ile Thr Val Tyr Arg Trp Cys Gly Met Ala Glu Phe Gly
    290                 295                 300

Tyr Gln Ile Ser Asp Pro Leu Pro Ser Leu Lys Glu Met Glu Glu Lys
305                 310                 315                 320

Phe Leu Asn Thr Met Lys Glu Asp Lys Gly Tyr Met Ser Thr Ser Leu
                325                 330                 335

Ser Ser Glu Arg Leu Ser Ala Phe Gly Ser Arg Lys Phe Ile Leu Arg
            340                 345                 350

Leu Gln Val Pro Lys Gly Ser Thr Gly Ala Tyr Leu Ser Ala Ile Gly
        355                 360                 365

Gly Phe Ala Ser Glu Lys Glu Ile Leu Ile Asp Lys Asp Ser Asn Tyr
    370                 375                 380

His Ile Asp Lys Ile Thr Glu Val Val Ile Lys Gly Val Lys Arg Tyr
385                 390                 395                 400

Val Val Asp Ala Thr Leu Leu Thr Lys
                405

<210> SEQ ID NO 9
<211> LENGTH: 2520
<212> TYPE: DNA
<213> ORGANISM: Artificial Sequence
<220> FEATURE:
<223> OTHER INFORMATION: modified DNA encoding ISP1A protein
<220> FEATURE:
<221> NAME/KEY: CDS
<222> LOCATION: (3)..(2510)

<400> SEQUENCE: 9 cc atg gct atc gcc acc acc acc cag gct tcg aag gac aac cag atc          47
   Met Ala Ile Ala Thr Thr Thr Gln Ala Ser Lys Asp Asn Gln Ile
   1               5                   10                  15 gac agg gag ggc ctg ctg ggc tac tac ttc aag ggc aag gac ttc aac          95
Asp Arg Glu Gly Leu Leu Gly Tyr Tyr Phe Lys Gly Lys Asp Phe Asn
                20                  25                  30 gac ctg acc ctg ttc gct cca acc agg gac aac acc ctg atc tac gac         143
Asp Leu Thr Leu Phe Ala Pro Thr Arg Asp Asn Thr Leu Ile Tyr Asp
            35                  40                  45 cag cag acc gct aac acc ctc gtg gac cag aag cac cag gag tac cac         191
Gln Gln Thr Ala Asn Thr Leu Val Asp Gln Lys His Gln Glu Tyr His
        50                  55                  60 tcc atc cgc tgg atc ggc ctg atc cag tcc tcc gcc act ggt gac ttc         239
Ser Ile Arg Trp Ile Gly Leu Ile Gln Ser Ser Ala Thr Gly Asp Phe
    65                  70                  75
```

```
acc ttc aag ctg tcc gac gac gag aac gcc atc atc gag ctg gac ggc    287
Thr Phe Lys Leu Ser Asp Asp Glu Asn Ala Ile Ile Glu Leu Asp Gly
 80              85                  90                  95 aag gtg atc tcc gag aag ggc aac aac aag cag tcc gtg cac ctc gaa    335
Lys Val Ile Ser Glu Lys Gly Asn Asn Lys Gln Ser Val His Leu Glu
                    100                 105                 110 aag ggc cag ctg gtg cag atc aag atc gag tac cag tcc gac gac gcc    383
Lys Gly Gln Leu Val Gln Ile Lys Ile Glu Tyr Gln Ser Asp Asp Ala
                        115                 120                 125 ctg cac atc gac aac aag atc ttc aag gag ctg aag ctg ttc aag atc    431
Leu His Ile Asp Asn Lys Ile Phe Lys Glu Leu Lys Leu Phe Lys Ile
                130                 135                 140 gac tcc cag aac cac tcc cag cag gtg cag cag gac gag ctg agg aac    479
Asp Ser Gln Asn His Ser Gln Gln Val Gln Gln Asp Glu Leu Arg Asn
145                 150                 155 cca gag ttc aac aag aag gag acc cag gtg ttc ctg aag aag gcc tcc    527
Pro Glu Phe Asn Lys Lys Glu Thr Gln Val Phe Leu Lys Lys Ala Ser
160                 165                 170                 175 aag acc aac ctg ttc acc cag aag acc aag agg gac atc gac gag gac    575
Lys Thr Asn Leu Phe Thr Gln Lys Thr Lys Arg Asp Ile Asp Glu Asp
                180                 185                 190 acc gac acc gac ggc gac tcc atc ccg gac gtg tgg gag gag aac ggc    623
Thr Asp Thr Asp Gly Asp Ser Ile Pro Asp Val Trp Glu Glu Asn Gly
                195                 200                 205 tac acc atc cag aac aag gtg gcc gtg aag tgg gac gac tcc ctg gcc    671
Tyr Thr Ile Gln Asn Lys Val Ala Val Lys Trp Asp Asp Ser Leu Ala
                210                 215                 220 tcc aag ggc tac cag aag ttc acc agc aac cca ctc gaa gcc cac acc    719
Ser Lys Gly Tyr Gln Lys Phe Thr Ser Asn Pro Leu Glu Ala His Thr
    225                 230                 235 gtg ggc gac cca tac tcc gac tac gag aag gct gct agg gac atg cca    767
Val Gly Asp Pro Tyr Ser Asp Tyr Glu Lys Ala Ala Arg Asp Met Pro
240                 245                 250                 255 ctg tcc aac gcc aag gag acc ttc aac cca ctg gtg gct gct ttc cca    815
Leu Ser Asn Ala Lys Glu Thr Phe Asn Pro Leu Val Ala Ala Phe Pro
                260                 265                 270 tcc gtg aac gtg tcc ctc gaa aag gtg atc ctg tcc aag aac gag gac    863
Ser Val Asn Val Ser Leu Glu Lys Val Ile Leu Ser Lys Asn Glu Asp
                275                 280                 285 ctg tcc cac tcc gtg gag tcc tcc cag tcc acc aac tgg tcc tac acc    911
Leu Ser His Ser Val Glu Ser Ser Gln Ser Thr Asn Trp Ser Tyr Thr
    290                 295                 300 aac acc gag ggc gtg aac gtg aac gct ggt tgg tcc ggt ctg ggt cca    959
Asn Thr Glu Gly Val Asn Val Asn Ala Gly Trp Ser Gly Leu Gly Pro
305                 310                 315 tcc ttc ggc gtg tcc gtg aac tac cag cac tcc gag acc gtg gcc aac   1007
Ser Phe Gly Val Ser Val Asn Tyr Gln His Ser Glu Thr Val Ala Asn
320                 325                 330                 335 gag tgg ggc tcc gcc acc aac gac ggc acc cac atc aac ggt gct gag   1055
Glu Trp Gly Ser Ala Thr Asn Asp Gly Thr His Ile Asn Gly Ala Glu
                340                 345                 350 tcc gcc tac ctg aac gcc aac gtg agg tac aac aac gtg ggc acc ggt   1103
Ser Ala Tyr Leu Asn Ala Asn Val Arg Tyr Asn Asn Val Gly Thr Gly
                355                 360                 365 gct atc tac gag acc aag cca acc acc tcc ttc atc ctg gac ggc acc   1151
Ala Ile Tyr Glu Thr Lys Pro Thr Thr Ser Phe Ile Leu Asp Gly Thr
                370                 375                 380 acc atc ggc acc atc aag gcc aag gag aac acc acc gct ctg acc atc   1199
Thr Ile Gly Thr Ile Lys Ala Lys Glu Asn Thr Thr Ala Leu Thr Ile
385                 390                 395
```

-continued

| | | |
|---|---|---|
| ctg cca gac cag tcc tac cca gag aag ggc aag aac ggc atc gcc atc<br>Leu Pro Asp Gln Ser Tyr Pro Glu Lys Gly Lys Asn Gly Ile Ala Ile<br>400                         405                     410                   415 | 1247 |

| aac acg atg gac gac ttc aac tcc agg ccg atc cca ctg aac aag gag<br>Asn Thr Met Asp Asp Phe Asn Ser Arg Pro Ile Pro Leu Asn Lys Glu<br>                    420                   425                        430 | 1295 |

| cag ctg aac acc tac ctg tcc aac aag aag ccg atc ctg ctc gaa acc<br>Gln Leu Asn Thr Tyr Leu Ser Asn Lys Lys Pro Ile Leu Leu Glu Thr<br>           435                   440                     445 | 1343 |

| gac cag gtg gag ggc aag tac gcc atc aag gac acc aac ggc aac atc<br>Asp Gln Val Glu Gly Lys Tyr Ala Ile Lys Asp Thr Asn Gly Asn Ile<br>450                         455                     460 | 1391 |

| acc atc gct ggt gac tgg aac ggc atc acc gac gag atc tcc gcc aag<br>Thr Ile Ala Gly Asp Trp Asn Gly Ile Thr Asp Glu Ile Ser Ala Lys<br>465                        470                     475 | 1439 |

| acc gcc agc atc atc gtc gac aac ggc aac cag atg tcc gag aag agg<br>Thr Ala Ser Ile Ile Val Asp Asn Gly Asn Gln Met Ser Glu Lys Arg<br>480                         485                   490                   495 | 1487 |

| gtg gct gct aag gac tac acc aac cca gag gac aag acc cca aat tta<br>Val Ala Ala Lys Asp Tyr Thr Asn Pro Glu Asp Lys Thr Pro Asn Leu<br>                   500                     505                    510 | 1535 |

| tcc gtg aag gag gcc ctg aag ctg gcc tac cca gac gag atc gag gag<br>Ser Val Lys Glu Ala Leu Lys Leu Ala Tyr Pro Asp Glu Ile Glu Glu<br>           515                   520                     525 | 1583 |

| aag gac ggc ctg ctg ttc tac aac gac cag ccg atc ttc gag gct tcc<br>Lys Asp Gly Leu Leu Phe Tyr Asn Asp Gln Pro Ile Phe Glu Ala Ser<br>530                         535                     540 | 1631 |

| gtg cag tcc tac gtg gac gag tac acc gct aag cag atc agg aag cag<br>Val Gln Ser Tyr Val Asp Glu Tyr Thr Ala Lys Gln Ile Arg Lys Gln<br>545                        550                   555 | 1679 |

| ctg aac gac tcc acc ggt tcc ttc aag gac gtg aag aac ctg tac gac<br>Leu Asn Asp Ser Thr Gly Ser Phe Lys Asp Val Lys Asn Leu Tyr Asp<br>560                       565                     570                   575 | 1727 |

| gtg aag ctc gaa ccg aag atg aac ttc aca ata aag acc tcc acc ctg<br>Val Lys Leu Glu Pro Lys Met Asn Phe Thr Ile Lys Thr Ser Thr Leu<br>                   580                     585                   590 | 1775 |

| tac gac ggt ggt gag tcc gac aac acc aag atc ggc aac tgg tac tac<br>Tyr Asp Gly Gly Glu Ser Asp Asn Thr Lys Ile Gly Asn Trp Tyr Tyr<br>          595                   600                     605 | 1823 |

| acc tac gtg gtg aac ggt ggt aac acc ggt aag aag cag tac agg tcc<br>Thr Tyr Val Val Asn Gly Gly Asn Thr Gly Lys Lys Gln Tyr Arg Ser<br>                   610                   615                   620 | 1871 |

| gct aac aag ggt gct ttc acc gag ctg tcc acc gag tcc aag aac aag<br>Ala Asn Lys Gly Ala Phe Thr Glu Leu Ser Thr Glu Ser Lys Asn Lys<br>625                        630                     635 | 1919 |

| ctg aag aag aac atc gac tac tac gtg tcc ctg tac atg aag gct gac<br>Leu Lys Lys Asn Ile Asp Tyr Tyr Val Ser Leu Tyr Met Lys Ala Asp<br>640                         645                   650                   655 | 1967 |

| tcc aag gtg tcc gtg gac atc gag atc gac ggt aag cag gag tcc atc<br>Ser Lys Val Ser Val Asp Ile Glu Ile Asp Gly Lys Gln Glu Ser Ile<br>                   660                   665                   670 | 2015 |

| gtg acc gac aac atc acc ctg gac cac gtg ggt tac cag agg atc aac<br>Val Thr Asp Asn Ile Thr Leu Asp His Val Gly Tyr Gln Arg Ile Asn<br>675                        680                     685 | 2063 |

| atc ctg gtg cca aac ctg gag ggc aac gag atc aac acc atc tcc atc<br>Ile Leu Val Pro Asn Leu Glu Gly Asn Glu Ile Asn Thr Ile Ser Ile<br>          690                   695                   700 | 2111 |

| aag ggt gac ggc cag acc aac gtg tac tgg gac gac gtg tcc ttc gtg<br>Lys Gly Asp Gly Gln Thr Asn Val Tyr Trp Asp Asp Val Ser Phe Val<br>705                        710                     715 | 2159 |

```
gag gtg ggt gct gag gag atc gag tac aag gac cca gtg cca cag ttc      2207
Glu Val Gly Ala Glu Glu Ile Glu Tyr Lys Asp Pro Val Pro Gln Phe
720                 725                 730                 735 gac atc atc gag ggt gac ttc gac ttc ttc ggt gac cca ctg gcc gtg      2255
Asp Ile Ile Glu Gly Asp Phe Asp Phe Phe Gly Asp Pro Leu Ala Val
                740                 745                 750 aag tac cac gac gct acc tac ttc atc gac tcc cca ctg att acc cag      2303
Lys Tyr His Asp Ala Thr Tyr Phe Ile Asp Ser Pro Leu Ile Thr Gln
            755                 760                 765 acc cca ggt acc ttc tcc ttc acc tac aag gtg atc ggt gag cag acc      2351
Thr Pro Gly Thr Phe Ser Phe Thr Tyr Lys Val Ile Gly Glu Gln Thr
        770                 775                 780 aag acc gtg ctg gac tcc ggt tcc ggc aag aac gct aac agg atc aac      2399
Lys Thr Val Leu Asp Ser Gly Ser Gly Lys Asn Ala Asn Arg Ile Asn
    785                 790                 795 ctg gac ttc aag aac gtg aag tcc gac agg tcc ttc ctg tac acc ctg      2447
Leu Asp Phe Lys Asn Val Lys Ser Asp Arg Ser Phe Leu Tyr Thr Leu
800                 805                 810                 815 tcc tgc aag gac gac ctg tgg ggc tcc acc agg acc gct gtg gtg agg      2495
Ser Cys Lys Asp Asp Leu Trp Gly Ser Thr Arg Thr Ala Val Val Arg
                820                 825                 830 atc ttc gct gtg gac tgaggctagc                                       2520
Ile Phe Ala Val Asp
            835

<210> SEQ ID NO 10
<211> LENGTH: 836
<212> TYPE: PRT
<213> ORGANISM: Artificial Sequence
<220> FEATURE:
<223> OTHER INFORMATION: ISP1A protein

<400> SEQUENCE: 10

Met Ala Ile Ala Thr Thr Thr Gln Ala Ser Lys Asp Asn Gln Ile Asp
1               5                   10                  15

Arg Glu Gly Leu Leu Gly Tyr Tyr Phe Lys Gly Lys Asp Phe Asn Asp
            20                  25                  30

Leu Thr Leu Phe Ala Pro Thr Arg Asp Asn Thr Leu Ile Tyr Asp Gln
        35                  40                  45

Gln Thr Ala Asn Thr Leu Val Asp Gln Lys His Gln Glu Tyr His Ser
    50                  55                  60

Ile Arg Trp Ile Gly Leu Ile Gln Ser Ser Ala Thr Gly Asp Phe Thr
65                  70                  75                  80

Phe Lys Leu Ser Asp Asp Glu Asn Ala Ile Ile Glu Leu Asp Gly Lys
                85                  90                  95

Val Ile Ser Glu Lys Gly Asn Asn Lys Gln Ser Val His Leu Glu Lys
            100                 105                 110

Gly Gln Leu Val Gln Ile Lys Ile Glu Tyr Gln Ser Asp Asp Ala Leu
        115                 120                 125

His Ile Asp Asn Lys Ile Phe Lys Glu Leu Lys Leu Phe Lys Ile Asp
    130                 135                 140

Ser Gln Asn His Ser Gln Gln Val Gln Gln Asp Glu Leu Arg Asn Pro
145                 150                 155                 160

Glu Phe Asn Lys Lys Glu Thr Gln Val Phe Leu Lys Lys Ala Ser Lys
                165                 170                 175

Thr Asn Leu Phe Thr Gln Lys Thr Lys Arg Asp Ile Asp Glu Asp Thr
            180                 185                 190

Asp Thr Asp Gly Asp Ser Ile Pro Asp Val Trp Glu Glu Asn Gly Tyr
        195                 200                 205
```

```
Thr Ile Gln Asn Lys Val Ala Val Lys Trp Asp Asp Ser Leu Ala Ser
    210                 215                 220
Lys Gly Tyr Gln Lys Phe Thr Ser Asn Pro Leu Glu Ala His Thr Val
225                 230                 235                 240
Gly Asp Pro Tyr Ser Asp Tyr Glu Lys Ala Ala Arg Asp Met Pro Leu
                245                 250                 255
Ser Asn Ala Lys Glu Thr Phe Asn Pro Leu Val Ala Ala Phe Pro Ser
            260                 265                 270
Val Asn Val Ser Leu Glu Lys Val Ile Leu Ser Lys Asn Glu Asp Leu
        275                 280                 285
Ser His Ser Val Glu Ser Gln Ser Thr Asn Trp Ser Tyr Thr Asn
    290                 295                 300
Thr Glu Gly Val Asn Val Asn Ala Gly Trp Ser Gly Leu Gly Pro Ser
305                 310                 315                 320
Phe Gly Val Ser Val Asn Tyr Gln His Ser Glu Thr Val Ala Asn Glu
                325                 330                 335
Trp Gly Ser Ala Thr Asn Asp Gly Thr His Ile Asn Gly Ala Glu Ser
            340                 345                 350
Ala Tyr Leu Asn Ala Asn Val Arg Tyr Asn Asn Val Gly Thr Gly Ala
        355                 360                 365
Ile Tyr Glu Thr Lys Pro Thr Thr Ser Phe Ile Leu Asp Gly Thr Thr
    370                 375                 380
Ile Gly Thr Ile Lys Ala Lys Glu Asn Thr Thr Ala Leu Thr Ile Leu
385                 390                 395                 400
Pro Asp Gln Ser Tyr Pro Glu Lys Gly Lys Asn Gly Ile Ala Ile Asn
                405                 410                 415
Thr Met Asp Asp Phe Asn Ser Arg Pro Ile Pro Leu Asn Lys Glu Gln
            420                 425                 430
Leu Asn Thr Tyr Leu Ser Asn Lys Lys Pro Ile Leu Leu Glu Thr Asp
        435                 440                 445
Gln Val Glu Gly Lys Tyr Ala Ile Lys Asp Thr Asn Gly Asn Ile Thr
    450                 455                 460
Ile Ala Gly Asp Trp Asn Gly Ile Thr Asp Glu Ile Ser Ala Lys Thr
465                 470                 475                 480
Ala Ser Ile Ile Val Asp Asn Gly Asn Gln Met Ser Glu Lys Arg Val
                485                 490                 495
Ala Ala Lys Asp Tyr Thr Asn Pro Glu Asp Lys Thr Pro Asn Leu Ser
            500                 505                 510
Val Lys Glu Ala Leu Lys Leu Ala Tyr Pro Asp Glu Ile Glu Glu Lys
        515                 520                 525
Asp Gly Leu Leu Phe Tyr Asn Asp Gln Pro Ile Phe Glu Ala Ser Val
    530                 535                 540
Gln Ser Tyr Val Asp Glu Tyr Thr Ala Lys Gln Ile Arg Lys Gln Leu
545                 550                 555                 560
Asn Asp Ser Thr Gly Ser Phe Lys Asp Val Lys Asn Leu Tyr Asp Val
                565                 570                 575
Lys Leu Glu Pro Lys Met Asn Phe Thr Ile Lys Thr Ser Thr Leu Tyr
            580                 585                 590
Asp Gly Gly Glu Ser Asp Asn Thr Lys Ile Gly Asn Trp Tyr Tyr Thr
        595                 600                 605
Tyr Val Val Asn Gly Gly Asn Thr Gly Lys Lys Gln Tyr Arg Ser Ala
    610                 615                 620
Asn Lys Gly Ala Phe Thr Glu Leu Ser Thr Glu Ser Lys Asn Lys Leu
625                 630                 635                 640
```

```
Lys Lys Asn Ile Asp Tyr Tyr Val Ser Leu Tyr Met Lys Ala Asp Ser
                645                 650                 655

Lys Val Ser Val Asp Ile Glu Ile Asp Gly Lys Gln Glu Ser Ile Val
            660                 665                 670

Thr Asp Asn Ile Thr Leu Asp His Val Gly Tyr Gln Arg Ile Asn Ile
        675                 680                 685

Leu Val Pro Asn Leu Glu Gly Asn Glu Ile Asn Thr Ile Ser Ile Lys
    690                 695                 700

Gly Asp Gly Gln Thr Asn Val Tyr Trp Asp Asp Val Ser Phe Val Glu
705                 710                 715                 720

Val Gly Ala Glu Glu Ile Glu Tyr Lys Asp Pro Val Pro Gln Phe Asp
                725                 730                 735

Ile Ile Glu Gly Asp Phe Asp Phe Phe Gly Asp Pro Leu Ala Val Lys
                740                 745                 750

Tyr His Asp Ala Thr Tyr Phe Ile Asp Ser Pro Leu Ile Thr Gln Thr
            755                 760                 765

Pro Gly Thr Phe Ser Phe Thr Tyr Lys Val Ile Gly Glu Gln Thr Lys
        770                 775                 780

Thr Val Leu Asp Ser Gly Ser Gly Lys Asn Ala Asn Arg Ile Asn Leu
785                 790                 795                 800

Asp Phe Lys Asn Val Lys Ser Asp Arg Ser Phe Leu Tyr Thr Leu Ser
                805                 810                 815

Cys Lys Asp Asp Leu Trp Gly Ser Thr Arg Thr Ala Val Val Arg Ile
                820                 825                 830

Phe Ala Val Asp
        835

<210> SEQ ID NO 11
<211> LENGTH: 6
<212> TYPE: PRT
<213> ORGANISM: Artificial Sequence
<220> FEATURE:
<223> OTHER INFORMATION: polypeptide linker

<400> SEQUENCE: 11

Arg Lys Arg Lys Arg Lys
              5

<210> SEQ ID NO 12
<211> LENGTH: 6
<212> TYPE: PRT
<213> ORGANISM: Artificial Sequence
<220> FEATURE:
<223> OTHER INFORMATION: polypeptide linker

<400> SEQUENCE: 12

Gly Gly Gly Gly Gly Gly
              5
```